(12) United States Patent
Ebata et al.

(10) Patent No.: US 8,043,786 B2
(45) Date of Patent: Oct. 25, 2011

(54) ACID GENERATORS, SULFONIC ACIDS, SULFONYL HALIDES, AND RADIATION SENSITIVE RESIN COMPOSITIONS

(75) Inventors: Satoshi Ebata, Tokyo (JP); Yong Wang, Tokyo (JP); Isao Nishimura, Tokyo (JP)

(73) Assignee: JSR Corporation, Tokyo (JP)

( * ) Notice: Subject to any disclaimer, the term of this patent is extended or adjusted under 35 U.S.C. 154(b) by 525 days.

(21) Appl. No.: 10/547,769

(22) PCT Filed: Feb. 20, 2004

(86) PCT No.: PCT/JP2004/001973
§ 371 (c)(1),
(2), (4) Date: Oct. 2, 2006

(87) PCT Pub. No.: WO2004/078703
PCT Pub. Date: Sep. 16, 2004

(65) Prior Publication Data
US 2007/0054214 A1 Mar. 8, 2007

(30) Foreign Application Priority Data
Mar. 5, 2003 (JP) ................................. 2003-059028

(51) Int. Cl.
G03F 7/039 (2006.01)
G03F 7/038 (2006.01)
C07C 317/04 (2006.01)
C07C 309/80 (2006.01)

(52) U.S. Cl. ..................... 430/270.1; 430/325; 430/326; 430/905; 430/910; 430/914; 430/921; 430/925; 568/35; 568/28; 568/29; 568/30; 568/31; 568/34; 568/36; 568/37; 562/100; 562/828; 562/832; 562/833; 562/834

(58) Field of Classification Search .................. None
See application file for complete search history.

(56) References Cited

U.S. PATENT DOCUMENTS 7,108,955 B2 * 9/2006 Iwasawa et al. ............. 430/270.1
7,288,359 B2 * 10/2007 Iwasawa et al. ............. 430/270.1

FOREIGN PATENT DOCUMENTS

| EP | 1270553 A2 | 1/2003 |
|---|---|---|
| JP | 2003-337416 A | 11/2003 |
| WO | WO 02/090423 A1 * | 11/2002 |

OTHER PUBLICATIONS

Derwent English abstract for JP 2003-337416.*
Machine-assisted English translation for JP 2003-337416 as provided by JPO.*
Derwent Publication Ltd., London, GB; XP002383267 & JP 2000 327654 A (JSR Corp), Abstract (2000).
Advances in Polymer Science, vol. 62, pp. 1-48 (1984).
Inorganic Chemistry, vol. 32, pp. 5007-5010 (1993).
J Photopolym. Sci. Tech., pp. 571-576 (1998).
J. Vac. Sci. Technol. B16(1), pp. 69-76, (1998).
Proc. SPIEL vol. 3333, pp. 313-323 (1998).
Proc. SPIEL vol. 3333, pp. 634-642 (1998).

* cited by examiner

Primary Examiner — Sin J. Lee
(74) Attorney, Agent, or Firm — Ditthavong Mori & Steiner, P.C.

(57) ABSTRACT

The invention provides novel acid generators which are unproblematic in combustibility and accumulation inside the human body and can generate acids having high acidities and high boiling points and exhibiting properly short diffusion lengths in resist coating films and which permit the formation of resist patterns excellent smoothness with little dependence on the denseness of a mask pattern; sulfonic acids generated from the acid generators; sulfonyl halides useful as raw material in the synthesis of the acid generators; and radiation-sensitive resin compositions containing the acid generators. The acid generators have structures represented by the general formula (I),

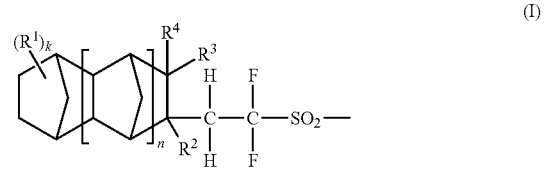

wherein $R^1$ is a monovalent substituent such as alkoxycarbonyl, alkylsulfonyl, or alkoxysulfonyl; $R^2$ to $R^4$ are each hydrogen or alkyl; k is an integer of 0 or above; and n is an integer of 0 to 5. Among the radiation-sensitive resin compositions, a positive one contains a resin having acid-dissociable groups in addition to the above acid generator, while a negative one contains an alkali-soluble resin and a crosslinking agent in addition to the acid generator.

3 Claims, 1 Drawing Sheet

ACID GENERATORS, SULFONIC ACIDS, SULFONYL HALIDES, AND RADIATION SENSITIVE RESIN COMPOSITIONS

TECHNICAL FIELD

The present invention relates to an acid generator, sulfonic acid, sulfonyl halide, and a radiation sensitive resin composition. More particularly, the present invention relates to a photoacid generator suitable for use in a positive-tone or negative-tone radiation sensitive resin composition which is used as a chemically amplified resist for microfabrication utilizing various types of radiation, for example, deep ultraviolet rays such as a KrF excimer laser, ArF excimer laser, $F_2$ excimer laser, or EUV (extreme ultraviolet), X-rays such as synchrotron radiation, or charged particle rays such as electron beams, to a sulfonic acid generated from said acid generator, to a sulfonyl halide useful as a raw material or intermediate for synthesizing said acid generator, and to a positive-tone or negative-tone radiation sensitive resin composition containing said acid generator.

BACKGROUND ART

In the field of microfabrication represented by fabrication of integrated circuit devices, a lithographic technology enabling microfabrication with a line width of 0.20 µm or less has been demanded in order to achieve higher integration.

A conventional lithographic process utilizes near ultraviolet rays such as i-line radiation. It is known in the art that microfabrication with a line width of a sub-quarter micron order using near ultraviolet rays is very difficult.

Therefore, use of radiation with a shorter wavelength has been studied for enabling microfabrication with a line width of 0.20 µm or less. As radiation with a shorter wavelength, deep ultraviolet rays represented by a line spectrum of a mercury lamp and an excimer laser, X-rays, electron beams, and the like can be given. Of these, a KrF excimer laser (wavelength: 248 nm), an ArF excimer laser (wavelength: 193 nm), an $F_2$ excimer laser (wavelength: 157 nm), EUV (wavelength 13 nm), and electron beams have attracted attention.

As a radiation sensitive resin composition applicable to the short wavelength radiations, a number of compositions utilizing a chemical amplification effect between a component having an acid-dissociable functional group and a photoacid generator which generates an acid upon irradiation (hereinafter called "exposure") has been proposed. Such a composition is hereinafter called a chemically-amplified radiation sensitive composition.

As the chemically-amplified radiation sensitive composition, Japanese Patent Publication No. 27660/1990 discloses a composition comprising a polymer containing a t-butyl ester group of carboxylic acid or a t-butylcarbonate group of phenol and a photoacid generator. This composition utilizes the effect of the polymer to release a t-butyl ester group or t-butyl carbonate group by the action of an acid generated upon exposure to form an acidic group such as a carboxylic group or a phenolic hydroxyl group, which renders an exposed area on a resist film readily soluble in an alkaline developer.

As characteristics demanded of a photoacid generator for a chemically-amplified radiation sensitive composition, superior transparency to radioactive rays, high quantum yield in acid generation, and capability of producing an acid exhibiting high acidity, high boiling point, and a suitable diffusion distance (hereinafter referred as diffusion length) in the resist film can be given.

To ensure high acidity, high boiling point, and appropriate diffusion length, the structure of an anionic moiety in the ionic photoacid generator and the structure of a sulfonyl moiety in the nonionic photoacid generator comprising a sulfonyl structure or a sulfonic acid ester structure are important. When the photoacid generator possesses a trifluoromethanesulfonyl structure, for example, even though a sufficiently strong acid to ensure adequate resolution performance of a photoresist is generated, there is a drawback of a high mask dependency due to the low boiling point and long diffusion length of the generated acid. When the photoacid generator possesses a sulfonyl structure with a large organic group such as a 10-camphorsulfonyl structure, even though the mask dependency is low due to the high boiling point and short diffusion length of the generated acid, the resolution performance as a photoresist is insufficient due to the poor acidity.

On the other hand, photoacid generators having a higher perfluoroalkylsulfonyl structure such as perfluoro-n-octane sulfonic acid (PFOS) have been given attention in recent years due to the adequate acidity, boiling point, and diffusion length.

However, the photoacid generators possessing a higher perfluoroalkylsulfonyl structure such as PFOS have environmental problems of low combustibility and accumulation in the human body. A regulation on their use has been proposed by the U.S. Environmental Protection Agency (see "Perfluorooctyl Sulfonates; Proposed Significant New Use Rule").

If a chemically amplified resist exhibiting poor film surface smoothness is used in devices with a design width on the order of a subhalf micron or less requiring a more precise line width control, irregularities (such as nano edge roughness) on the film surface is transferred to a substrate when a resist pattern is transferred to the substrate by an etching process or the like, giving rise to a decrease in pattern dimensional accuracy and impaired electric performance in the obtained devices (see, for example, J. Photopolym. Sci. Tech. p. 571-576 (1998); Proc. SPIE Vol. 3333, p 313-323(1998); Proc. SPIE Vol. 3333, p 634-642 (1998); and J. Vac. Sci. Technol. B16(1), p 69-76 (1998)). Therefore, in addition to exhibiting excellent resolution performance, chemically amplified radiation sensitive resin compositions are required to provide excellent surface smoothness after formation of the resist pattern.

For these reasons, there is an urgent need in the field of microfabrication for the development of an alternative component which can produce a chemically amplified radiation sensitive resin composition having no defects originating from the higher perfluoroalkane sulfonyl structure, excelling in resolution performance, and causing only slight nano edge roughness, and which also excels as a photoacid generator.

The object of the present invention is to provide a novel photoacid generator which exhibits high transparency to ultraviolet rays such as a KrF excimer laser, ArF excimer laser, $F_2$ excimer laser, or EUV, and electron beams, exhibits comparatively high combustibility and no bioaccumulation, produces an acid exhibiting high acidity, high boiling point, moderately short diffusion length in the resist film, and low dependency on the mask pattern density, and produces a resist pattern excelling in surface and sidewall smoothness; a sulfonic acid generated from the photoacid generator; a sulfonyl halide compound useful as a raw material or intermediate for synthesizing the photoacid generator; and a positive-tone or negative-tone radiation sensitive resin composition containing the photoacid generator.

DISCLOSURE OF THE INVENTION

First, the present invention provides an acid generator (hereinafter referred to as "acid generator (I)") which is a compound containing a structure represented by the following formula (I) (hereinafter referred to as "structure (I)"),

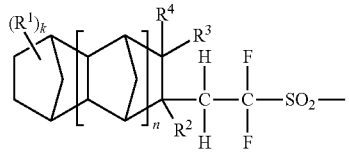

wherein $R^1$ represents —$R^5$, —$COR^6$, —$COOR^6$, —$CON(R^6)(R^7)$, —$N(R^6)(R^7)$, —$N(R^6)CO(R^7)$, —$N(R^6)COOR^7$, —$N(COR^6)(COR^7)$, —$SR^6$, —$SOR^6$, —$SO_2R^6$, or —$SO_2(OR^6)$ (wherein $R^5$ represents a substituted or unsubstituted, linear, branched, or cyclic monovalent hydrocarbon group having 1-30 carbon atoms, a substituted or unsubstituted aryl group having 6-30 carbon atoms, or a substituted or unsubstituted, monovalent hetero cyclic organic group having 4-30 carbon atoms, $R^6$ and $R^7$ individually represent a hydrogen atom, a substituted or unsubstituted, linear, branched, or cyclic monovalent hydrocarbon group having 1-30 carbon atoms, a substituted or unsubstituted aryl group having 6-30 carbon atoms, or substituted or unsubstituted, monovalent hetero cyclic organic group having 4-30 carbon atoms, provided that when both $R^6$ and $R^7$ are present in the group $R^1$, $R^6$ and $R^7$ may bond to form a ring), two or more $R^1$ groups, if present, may be either the same or different, $R^1$ group may bond to form a ring with carbon atoms in the norbornene structure, and two or more $R^1$ groups may bond to form a ring; $R^2$, $R^3$, and $R^4$ individually represent a hydrogen atom or a linear, branched, or cyclic alkyl group having 1-30 carbon atoms; k is an integer of 0 or more; and n is an integer of 0-5.

Second, the present invention provides a sulfonic acid represented by the following formula (I-a) (hereinafter referred to as "sulfonic acid (I-a)"),

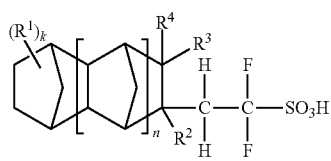

wherein $R^1$, $R^2$, $R^3$, $R^4$, k, and n are the same as defined for the formula (I).

Third, the present invention provides a sulfonyl halide compound represented by the following formula (I-b) (hereinafter referred to as "sulfonyl halide compound (I-b)"),

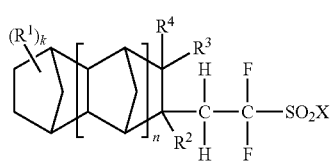

wherein $R^1$, $R^2$, $R^3$, $R^4$, k, and n are the same as defined for the formula (I) and X is a halogen atom.

Fourth, the present invention provides a positive-tone radiation sensitive resin composition comprising: (A) a photoacid generator comprising the acid generator (I) and (B) an acid-dissociable group-containing resin which is insoluble or scarcely soluble in alkali and becomes alkali soluble when the acid-dissociable group dissociates.

Fifth, the present invention provides a negative-tone radiation sensitive resin composition comprising: (A) a photoacid generator comprising the acid generator (I), (C) an alkali soluble resin, and (D) a compound that can crosslink the alkali soluble resin in the presence of an acid.

The present invention will now be described in more detail by way of embodiments.

Acid Generator (I)

The acid generator (I) is a component that generates a sulfonic acid (I-a) when subjected to exposure or heating.

Due to the presence of a fluorine-containing group having strong electron drawing capability in the α-position of the sulfonyl group in the structure (I), the sulfonic acid (I-a) produced by the acid generator (I) is highly acidic, is difficult to sublimate during photolithography processing due to a high boiling point, and has a moderately short acid diffusion length in the resist film. In addition, because the amount of fluorine in the sulfonic acid (I-a) is less than the amount of fluorine in the higher perfluoroalkyl sulfonic acid, combustibility is comparatively high and accumulation in the human body is low.

As examples of the unsubstituted linear, branched, or cyclic monovalent hydrocarbon group having 1-30 carbon atoms represented by $R^5$, $R^6$, and $R^7$ in the formula (I), alkyl groups such as a methyl group, ethyl group, n-propyl group, i-propyl group, n-butyl group, 1-methylpropyl group, 2-methylpropyl group, t-butyl group, n-pentyl group, i-pentyl group, 1,1-dimethylpropyl group, 1-methylbutyl group, 1,1-dimethylbutyl group, n-hexyl group, n-heptyl group, i-hexyl group, n-octyl group, i-octyl group, 2-ethylhexyl group, n-nonyl group, n-decyl group, n-undecyl group, n-dodecyl group, cyclopropyl group, cyclopentyl group, cyclohexyl group, and 4-t-butylcyclohexyl group; groups containing a cyclohexenyl group or norbornene skeleton; groups containing a norbornane group, groups containing an isobornyl skeleton, groups containing a tricyclodecane skeleton, groups containing a tetracyclododecane skeleton; groups containing an adamantine skeleton; and the like can be given.

As examples of substituents for the above hydrocarbon groups, an aryl group having 6-30 carbon atoms, a linear, branched, or cyclic alkenyl group having 2-30 carbon atoms, groups having 1-30 hetero atoms such as a halogen atom, oxygen atom, nitrogen atom, sulfur atom, phosphorus atom, and silicon atom; and the like can be given. These substituents may have any substituents, for example, one or more of the above-mentioned substituents.

As examples of the linear, branched, or cyclic monovalent hydrocarbon group having 1-30 carbon atoms substituted by the above substituents, a benzyl group, methoxymethyl group, methylthiomethyl group, ethoxymethyl group, ethylthiomethyl group, phenoxymethyl group, methoxycarbonylmethyl group, ethoxycarbonylmethyl group, acetylmethyl group, fluoromethyl group, trifluoromethyl group, chloromethyl group, trichloromethyl group, 2-fluoropropyl group, (trifluoroacetyl)methyl group, (trichloroacetyl)methyl group, (pentafluorobenzoyl)methyl group, aminomethyl group, (cyclohexylamino)methyl group, (diphenylphosphino)methyl group, (trimethylsilyl)methyl group, 2-phenylethyl group, 3-phenylpropyl group, 2-aminoethyl group, and the like can be given.

As examples of the unsubstituted aryl group having 6-30 carbon atoms for $R^5$, $R^6$, and $R^7$, a phenyl group, 1-naphthyl group, 2-naphthyl group, 1-anthryl group, 1-phenanthryl group, and the like can be given.

As examples of the unsubstituted monovalent heterocyclic organic group having 4-30 carbon atoms for $R^5$, $R^6$, and $R^7$, a furyl group, thienyl group, pyranyl group, pyrrolyl group, thianthrenyl group, pyrazolyl group, iso-thiazolyl group, iso-oxazolyl group, pyrazinyl group, pyrimidinyl group, pyridazinyl group, tetrahydropyranyl group, tetrahydrofuranyl group, tetrahydrothiopyranyl group, tetrahydrothiofuranyl group, 3-tetrahydrothiophen-1,1-dioxide group, and the like can be given.

As examples of substituents for the above aryl groups and monovalent heterocyclic organic groups, a linear, branched, or cyclic alkyl group having 1-30 carbon atoms, groups having 1-30 atoms including hetero atoms such as a halogen atom, oxygen atom, nitrogen atom, sulfur atom, phosphorus atom, and silicon atom; and the like can be given. These substituents may have any substituents, for example, one or more of the above-mentioned substituents.

As examples of the aryl group having 6-30 carbon atoms substituted by the above substituents, an o-tolyl group, m-tolyl group, p-tolyl group, p-hydroxyphenyl group, p-methoxyphenyl group, mesityl group, o-cumenyl group, 2,3-xylyl group, 2,4-xylyl group, 2,5-xylyl group, 2,6-xylyl group, 3,4-xylyl group, 3,5-xylyl group, p-fluorophenyl group, p-trifluoromethylphenyl group, p-chlorophenyl group, p-bromophenyl group, p-iodophenyl group, and the like can be given.

As examples of the monovalent heterocyclic organic group having 4-30 carbon atoms substituted with the above substituents, a 2-bromofuryl group, 3-methoxythienyl group, 3-bromotetrahydropyranyl group, 4-methoxytetrahydropyranyl group, 4-methoxytetrahydrothiopyranyl group, and the like can be given.

In the formula (I), $R^1$ groups may bond to any carbon atom in the norbornene structure except for the carbon atoms to which the $R^2$, $R^3$, and $R^4$ groups are bonded.

As examples of the linear, branched, or cyclic alkyl group having 1-30 carbon atoms represented by $R^2$, $R^3$, and $R^4$ in the formula (I), the same alkyl groups given as examples for the unsubstituted linear, branched, or cyclic monovalent hydrocarbon group having 1-30 carbon atoms represented by $R^5$, $R^6$, and $R^7$ can be given. The $R^2$, $R^3$, and $R^4$ groups may be the same or different.

As examples of $R^1$ in the formula (I), $-R^5$, $-COOR^6$, $-SR^6$, $-SOR^6$, $-SO_2R^6$, and $-SO_2(OR^6)$ are preferable, with $CH_3$, $-COOCH_3$, $-SCH_3$, $-SOCH_3$, $-SO_2CH_3$, and $-SO_2(OCH_3)$ being particularly preferable.

As examples for each of the $R^2$, $R^3$, and $R^4$ groups, a hydrogen atom and a linear or branched alkyl group having 1-5 carbon atoms are preferable, with a hydrogen atom, methyl group, ethyl group, and propyl group being particularly preferable.

In the formula (I), k is preferably 0-3 and n is preferably 0-1.

As specific preferable examples of the structure (I), structures shown by the following formulas (I-1) to (I-25) and the like can be given.

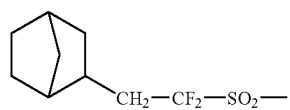

(I-1)

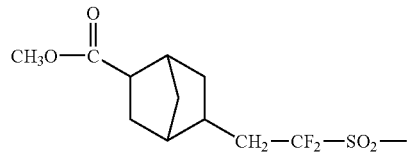

(I-2)

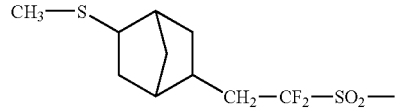

(I-3)

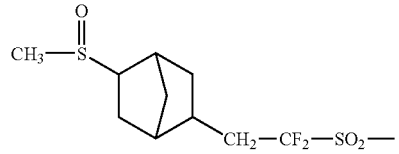

(I-4)

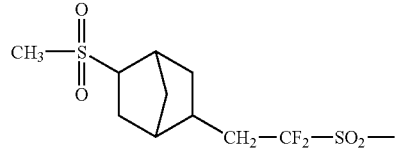

(I-5)

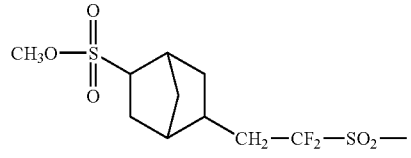

(I-6)

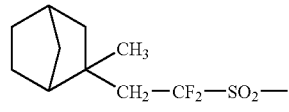

(I-7)

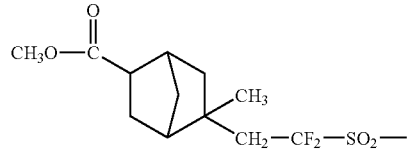

(I-8)

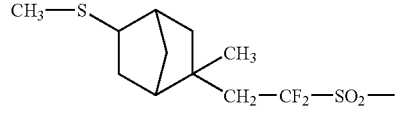

(I-9)

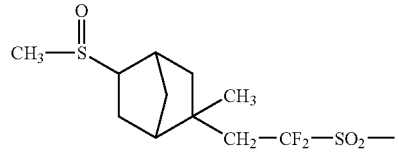

(I-10)

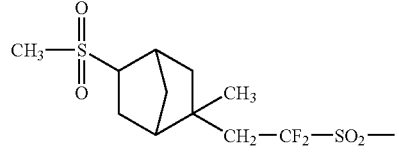

(I-11)

-continued (I-12) 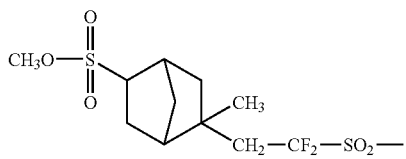

(I-13) 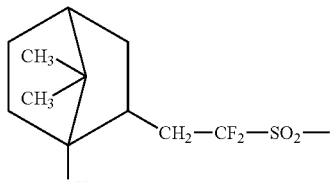

(I-14) 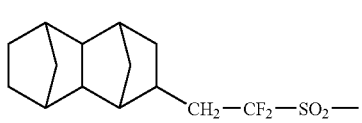

(I-15) 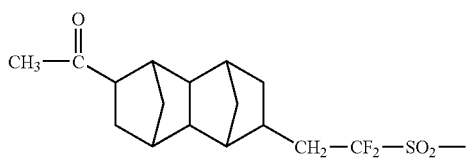

(I-16) 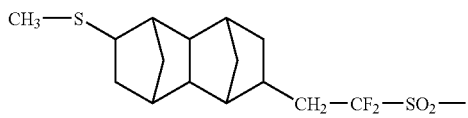

(I-17) 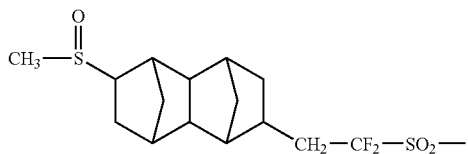

(I-18) 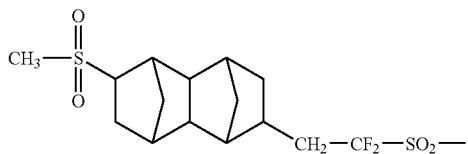

(I-19) 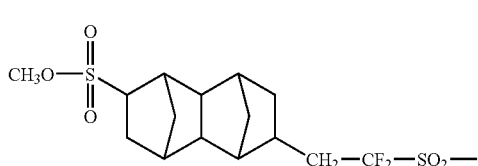

(I-20) 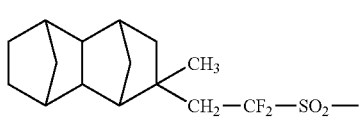

(I-21) 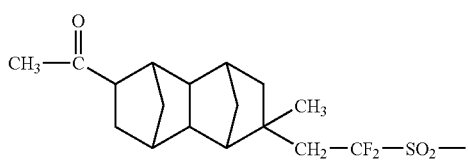

(I-22) 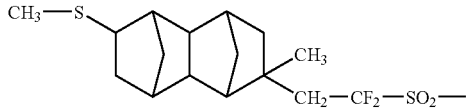

(I-23) 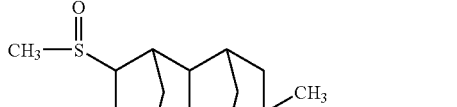

(I-24) 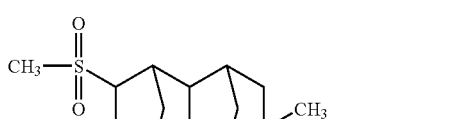

(I-25) 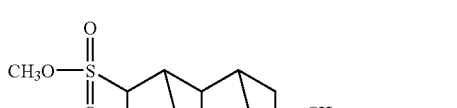

Of these structures (I), the structures shown by the formulas (A-1), (A-7), (A-14), and (A-20) are preferable.

As a preferable example of an ionic compound containing the structure (I), an onium sulfonate compound of the following formula (1) (hereinafter referred to as "onium sulfonate compound (1)") can be given.

The onium sulfonate compound (1) is a compound wherein the sulfonyl group of the structure (I) binds with an oxygen anion to form a sulfonic acid anion.

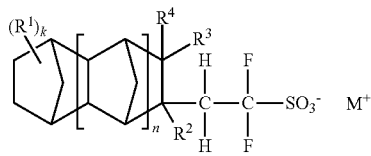  (1)

wherein $R^1$, $R^2$, $R^3$, $R^4$, k, and n are the same as defined for the formula (I) and $M^+$ represents a monovalent onium cation.

As examples of the monovalent onium cation represented by $M^+$, cations containing O, S, Se, N, P, As, Sb, Cl, Br, I, or the like can be given. Of these monovalent onium cations, S-containing cations and I-containing cations are preferable.

As examples of the S-containing cations and I-containing cations among the monovalent onium cations represented by $M^+$ in the formula (1), the cations represented by the following general formulas (i) and (ii) can be given.

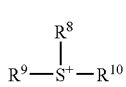  (i)

wherein $R^8$, $R^9$, and $R^{10}$ individually represent a substituted or unsubstituted, linear or branched alkyl group having 1-10 carbon atoms, or a substituted or unsubstituted aryl group having 6-18 carbon atoms, or two or more of $R^8$, $R^9$, and $R^{10}$ groups may bond to form a ring with the sulfur atom in the formula.

$$R^{11}-I^+-R^{12} \quad \text{(ii)}$$

wherein $R^{11}$ and $R^{12}$ individually represent a substituted or unsubstituted, linear or branched alkyl group having 1-10 carbon atoms, or a substituted or unsubstituted aryl group having 6-18 carbon atoms, or $R^{11}$ and $R^{12}$ may bond to form a ring in combination with the iodine atom in the formula.

The monovalent onium cation moiety of $M^+$ can be produced by a known method, for example, the method described in Advances in Polymer Science, Vol. 62, p. 1-48 (1984).

As examples of preferable monovalent onium cations, the sulfonium cations shown by the following formulas (i-1)-(i-64) and the iodonium cations shown by the following formulas (ii-1)-(ii-39) can be given.

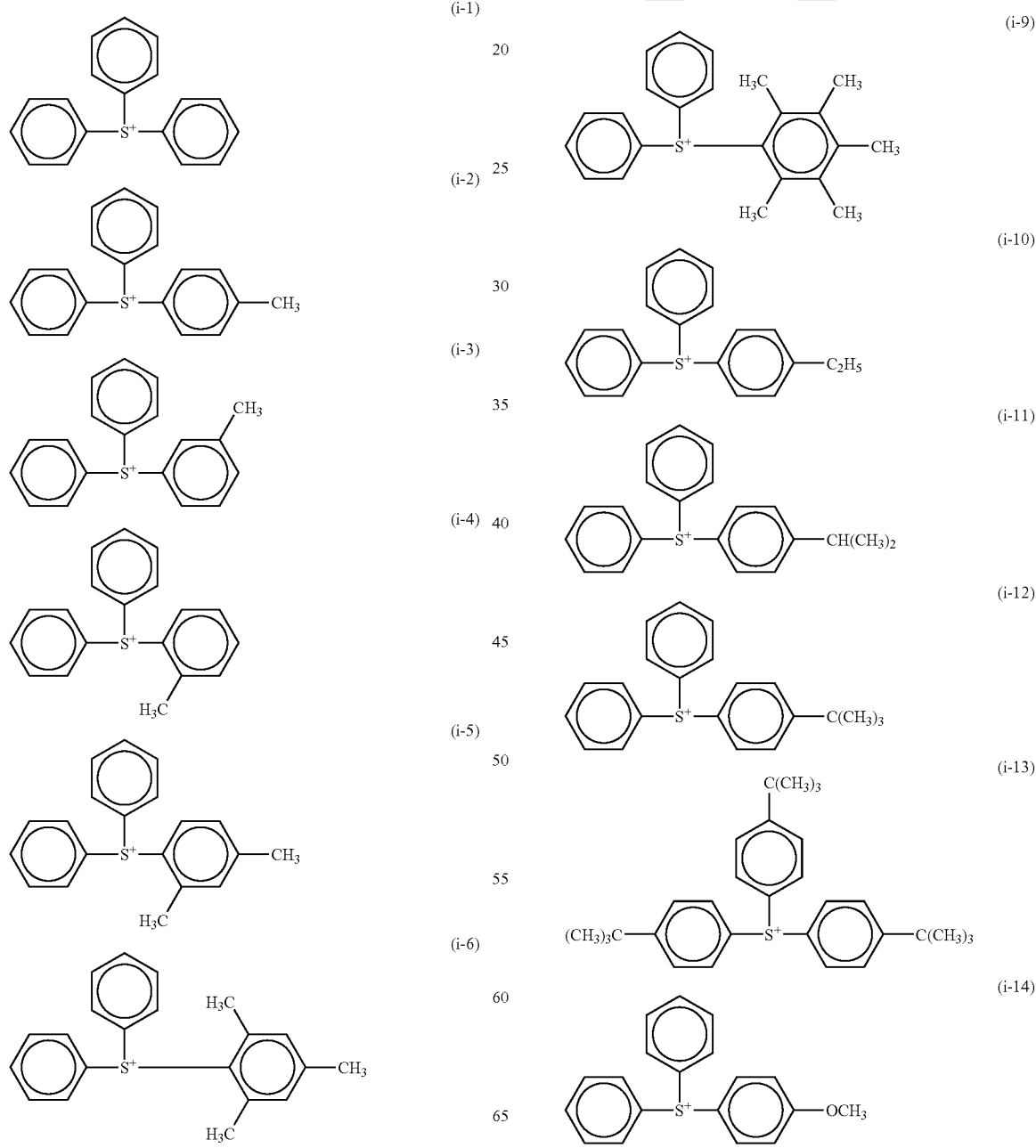

(i-15)
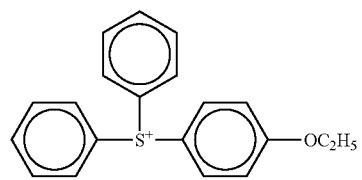
(i-16)
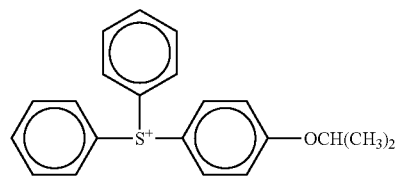
(i-17)
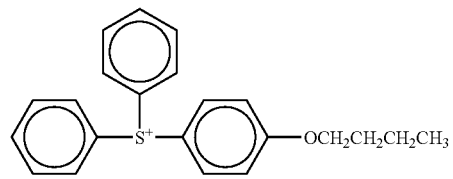
(i-18)
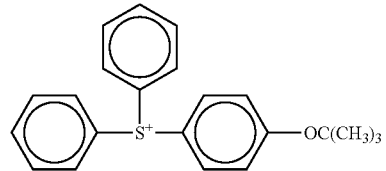
(i-19)
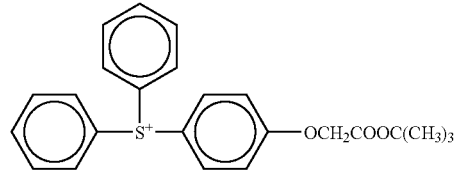
(i-20)
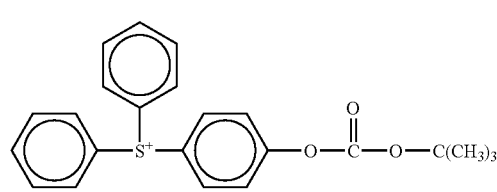
(i-21)
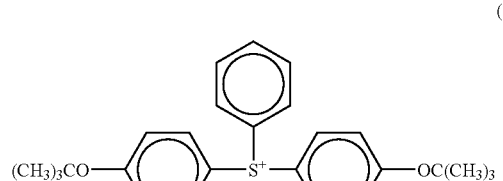
(i-22)
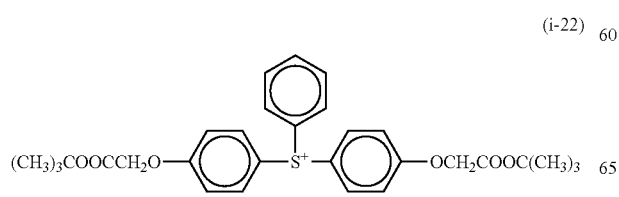
(i-23)
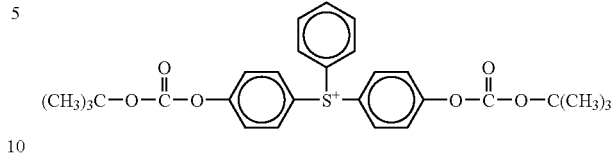
(i-24)
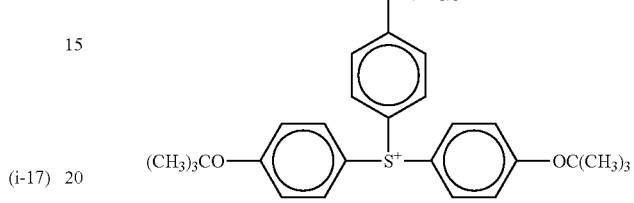
(i-25)
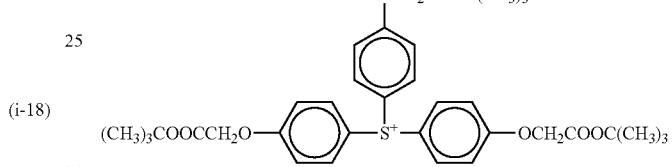
(i-26)
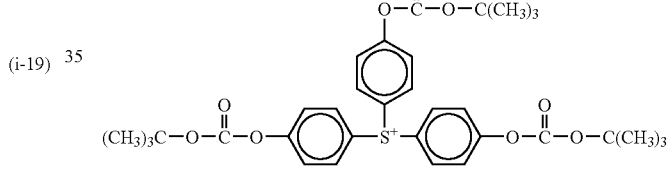
(i-27)
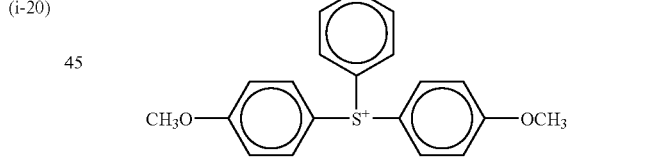
(i-28)
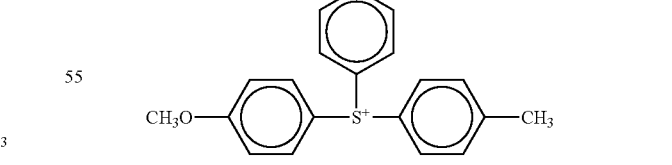
(i-29)
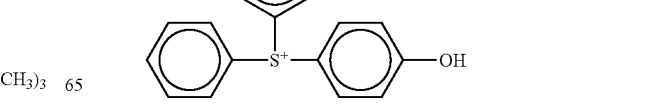

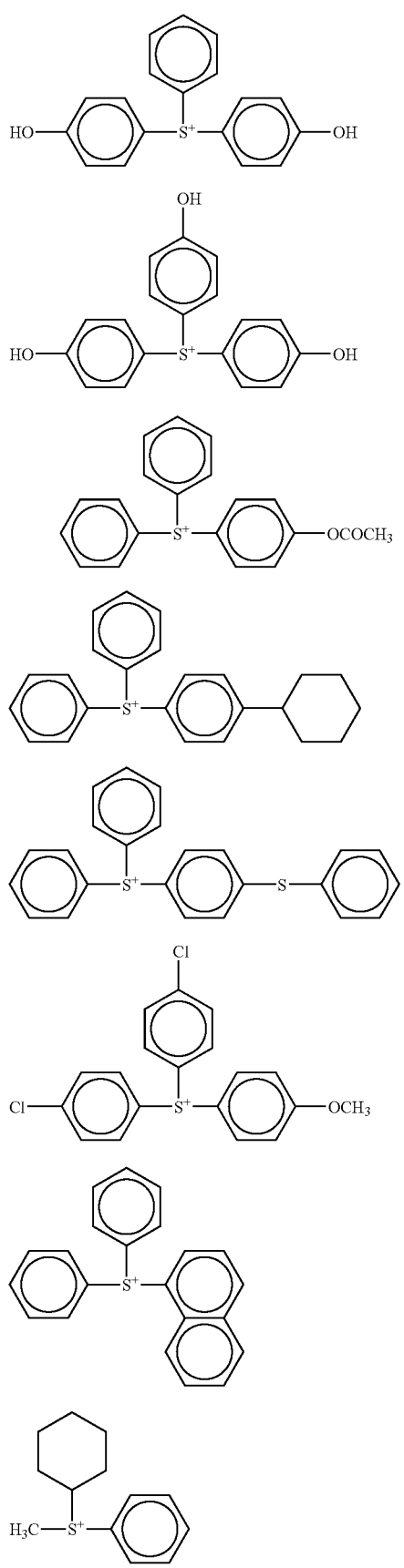

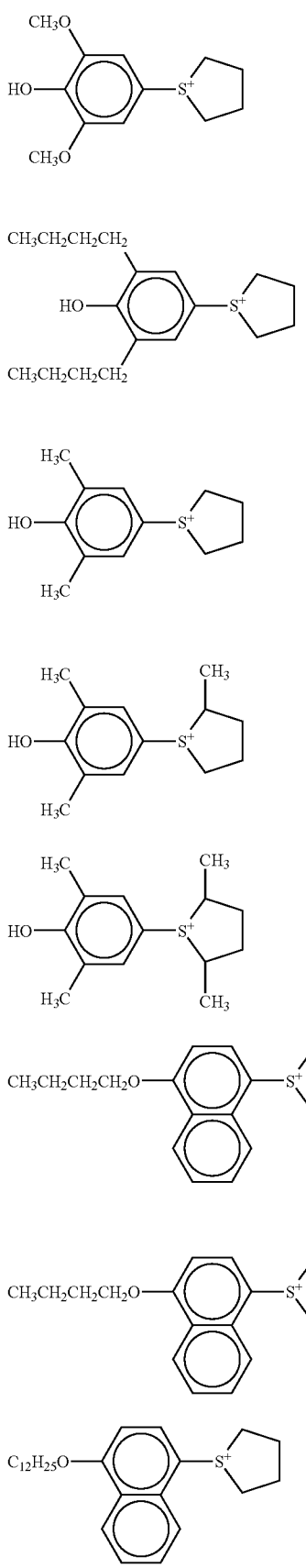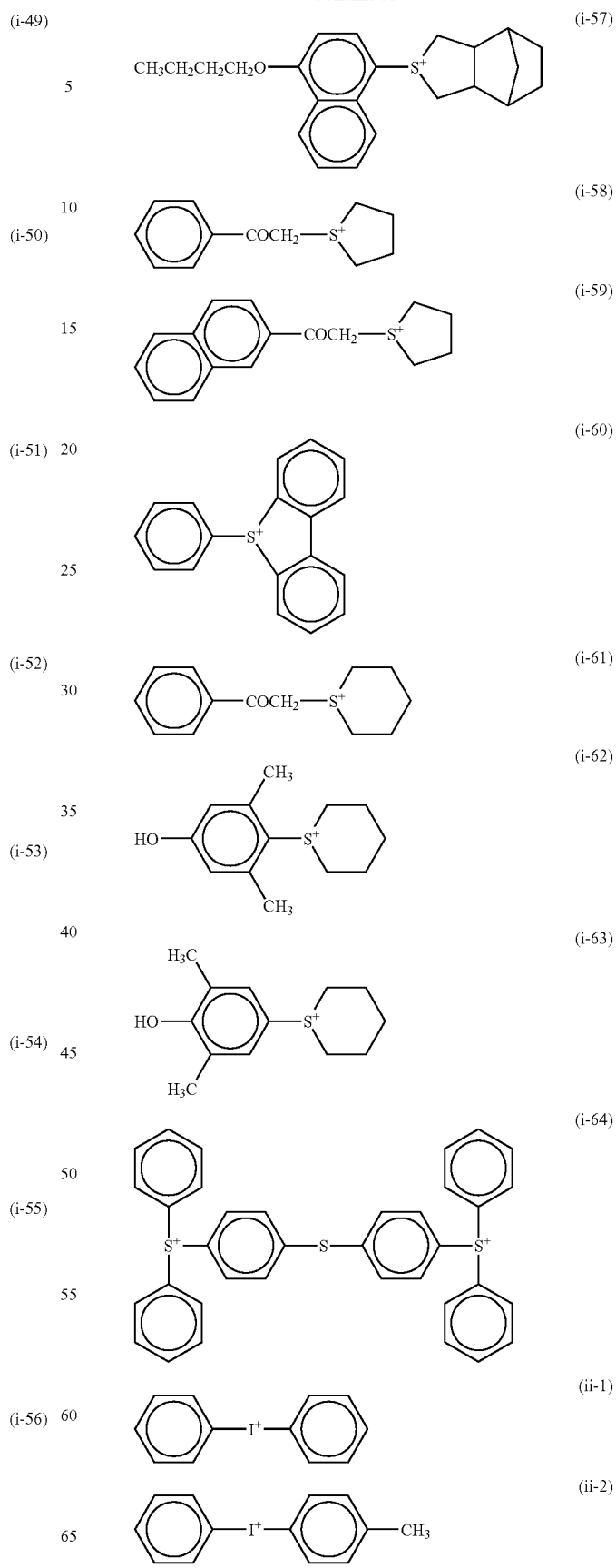

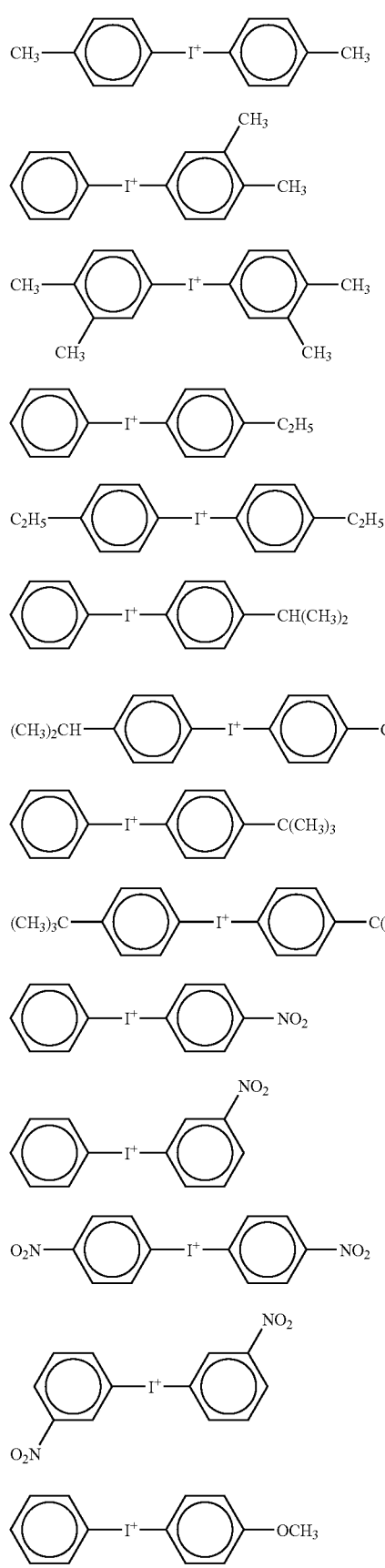
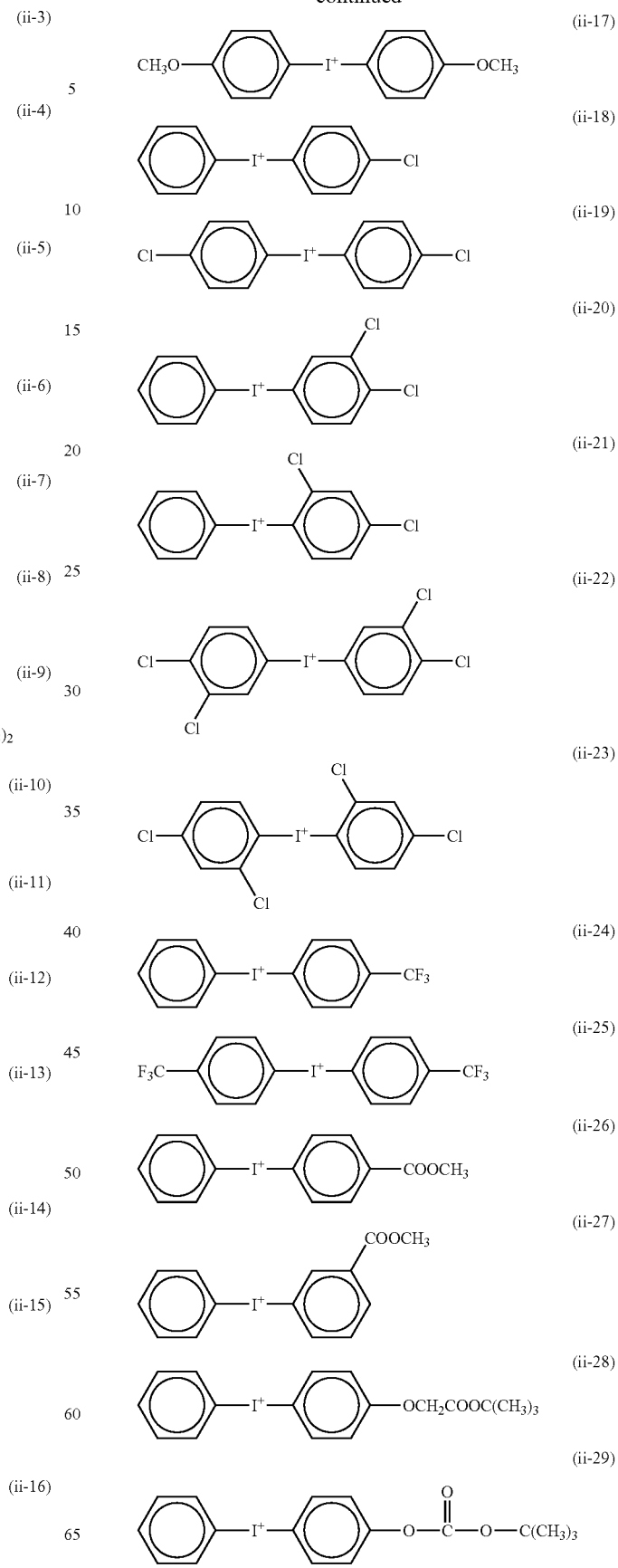

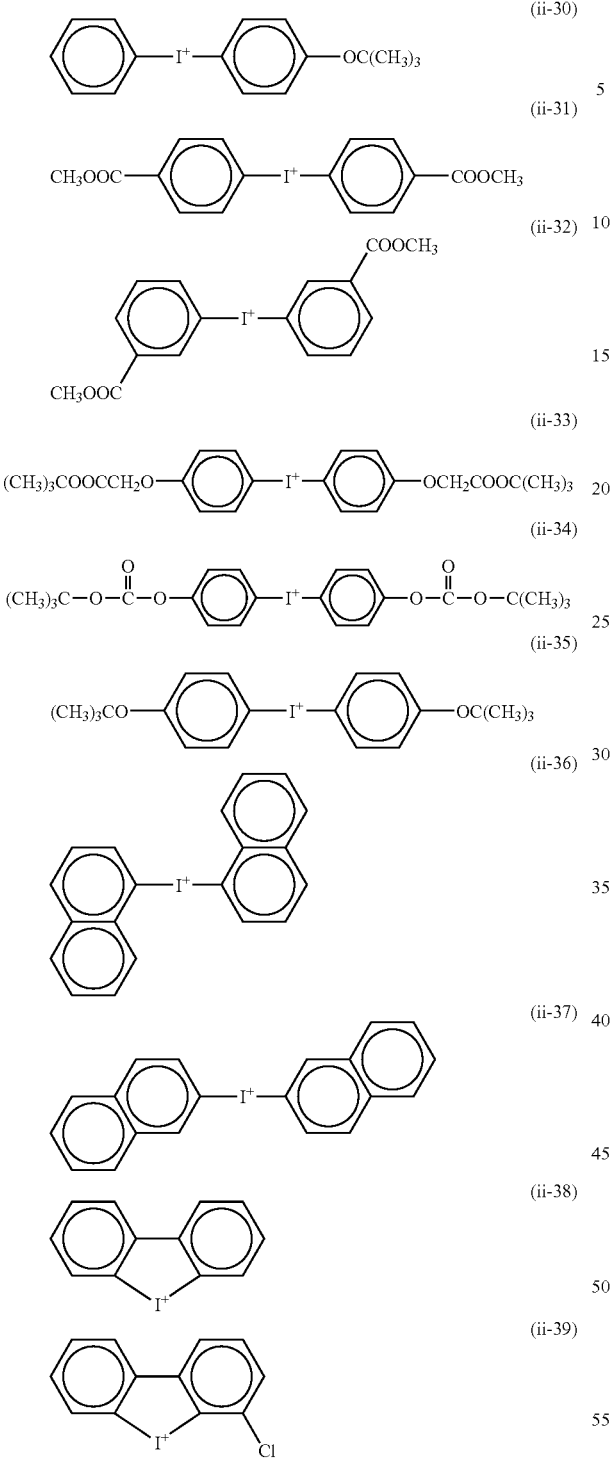

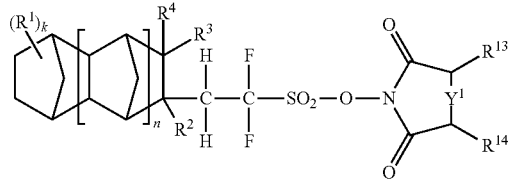

wherein $R^1$, $R^2$, $R^3$, $R^4$, k, and n are the same as defined for the formula (I), $R^{13}$ and $R^{14}$ individually represent a hydrogen atom or a substituted or unsubstituted monovalent organic group, or $R^{13}$ and $R^{14}$ may bond to form a ring together with the carbon atom to which the groups $R^{13}$ or $R^{14}$ bond, and $Y^1$ is a single bond, a double bond, or a divalent organic group.

As preferable imide groups for bonding with the sulfonyloxy group ($SO_2$—O—) of formula (2), the groups of the following formulas (2-1)-(2-9) can be given.

(2-1)

(2-2)

(2-3)

(2-4)

(2-5)

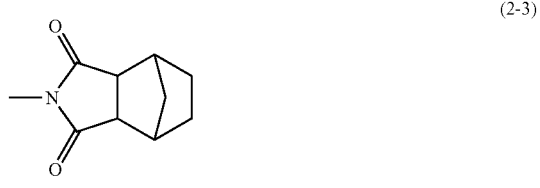

(2-6)

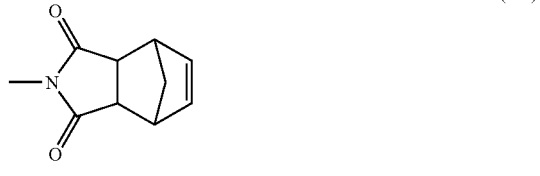

Of these monovalent onium cations, the sulfonium cations shown by the formulas (i-1), (i-2), (i-6), (i-8), (i-13), (i-19), (i-25), (i-27), (i-29), (i-51), and (i-54), and the iodonium cations shown by the formulas (ii-1) and (ii-11) are preferable.

As a preferable nonionic compound containing the structure (I), an N-sulfonyloximide compound of the following formula (2) (hereinafter referred to as "N-sulfonyloximide compound (2)") can be given.

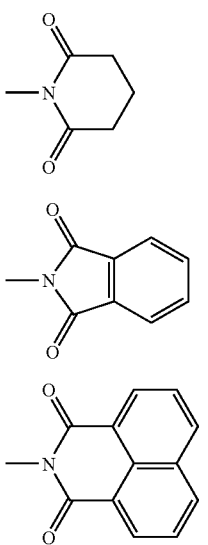

Of these groups, the groups of the formulas (2-1), (2-4), (2-8), or (2-9) are preferable.

The acid generator (I) generates a sulfonic acid (I-a) by exposure or heating and can be very suitably used as a photoacid generator in the later described positive-tone radiation sensitive resin composition and negative-tone radiation sensitive resin composition.

The process of manufacturing the onium sulfonate compound (1) will now be described in detail.

The onium sulfonate compound (1) can be produced by a common method, for example, the method described in Advances in Polymer Science, Vol. 62, p. 1-48 (1984) and Inorganic Chemistry, Vol. 32, p. 5007-5010 (1993).

Specifically, as shown by the following reaction formula (1), the precursor (1a) is caused to react with sodium dithionite in the presence of an inorganic base to produce sulfinate (1b). The sulfinate (1b) is then oxidized using hydrogen peroxide or the like to produce sulfonate (1c), which is ion-exchanged with a counter-ion exchange precursor $M^+Z^-$.

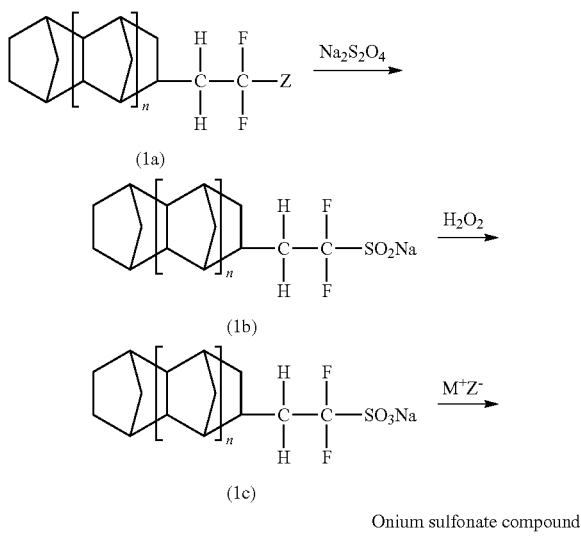

wherein Z is a releasable monovalent group and $Z^-$ is a monovalent anion.
(Description of the substituent bonded to the carbon atoms constituting the norbornene ring is omitted.)

As examples of the releasable monovalent group for Z of the precursor (1a), in addition to halogen atoms such as chlorine, bromine, and iodine, a methanesulfonate group, p-toluenesulfonate group, and the like can be given, with bromine and iodine atoms being preferable.

In the reaction of the precursor (1a) with sodium dithionite, the molar ratio of sodium dithionite to the precursor (1a) is usually 0.01-100 and preferably 1.0-10.

As examples of the inorganic base used in the reaction, lithium carbonate, sodium carbonate, potassium carbonate, lithium hydrogencarbonate, sodium hydrogencarbonate, potassium hydrogencarbonate, and the like can be given, with sodium hydrogencarbonate and potassium carbonate being preferable.

These inorganic bases may be used either individually or in combination of two or more.

The molar ratio of the inorganic base to the sodium dithionite is usually 1.0-10.0 and preferably 2.0-4.0.

This reaction is preferably carried out in a mixed solvent of an organic solvent and water. As the organic solvent, solvents possessing a high mutual solubility with water such as lower alcohols, tetrahydrofuran, N,N-dimethylformamide, N,N-dimethylacetoamide, acetonitrile, dimethylsulfoxide, and the like can be given as preferable examples, with N,N-dimethylacetoamide, acetonitrile, and dimethylsulfoxide being more preferable, and acetonitrile and dimethylsulfoxide being particularly preferable. These organic solvents may be used either individually or in combination of two or more.

The amount of the organic solvent in the total amount of the organic solvent and water is usually 5 parts by weight or more, preferably 10 parts by weight or more, and more preferably 20-90 parts by weight for 100 parts by weight of the total amount of the organic solvent and water.

The amount of the mixed solvent used is usually 5-100 parts by weight, preferably 10-100 parts by weight, and particularly preferably 20-90 parts by weight for 100 parts by weight of the precursor (1a).

The reaction is carried out at a temperature of usually 40-200° C., and preferably 60-120° C. for usually 0.5-72 hours, and preferably 2-24 hours. If the reaction temperature used is higher than the boiling point of the organic solvent or water, a pressure vessel such as an autoclave is used.

As the oxidizer used in the oxidation reaction of the sulfinate (1b), in addition to hydrogen peroxide, methachloroperbenzoic acid, t-butyl hydroperoxide, potassium peroxysulfate, potassium permanganate, sodium perborate, sodium metaiodate, chromic acid, sodium dichromate, halogen, iodobenzene dichloride, iodobenzene diacetate, osmium oxide (VII), ruthenium oxide (VII), sodium hypochlorite, sodium chlorite, oxygen gas, ozone gas, and the like can be given, with hydrogen peroxide, methachloroperbenzoic acid, and t-butyl hydroperoxide being preferable.

These oxidizers may be used either individually or in combination of two or more. The molar ratio of the oxidizer to the sulfinate (1b) is usually 1.0-10.0 and preferably 1.5-4.0.

Furthermore, a transition metal catalyst may be used together with the above-mentioned oxidizer.

As examples of the transition metal catalyst, disodium tungstate, iron (III) chloride, ruthenium (III) chloride, and selenium (IV) oxide can be given, with disodium tungstate being preferable.

These transition metal catalysts may be used either individually or in combination of two or more.

The molar ratio of the transition metal catalyst to the sulfinate (1b) is usually 0.001-2.0, preferably 0.01-1.0, and particularly preferably 0.03-0.5.

Furthermore, in addition to the above-mentioned oxidizer and transition metal catalyst, a buffer agent may be used for controlling the pH of the reaction solution.

As examples of the buffer agent, disodium hydrogenphosphate, sodium dihydrogenphosphate, dipotassium hydrogenphosphate, potassium dihydrogenphosphate, and the like can be given. These buffer agents may be used either individually or in combination of two or more. The molar ratio of the buffer agent to the sulfinate (1b) is usually 0.01-2.0, preferably 0.03-1.0, and particularly preferably 0.05-0.5.

This reaction is usually carried out in a reaction solvent.

As the reaction solvent, water, organic solvents such as lower alcohols, tetrahydrofuran, N,N-dimethylformamide, N,N-dimethylacetoamide, acetonitrile, dimethylsulfoxide, acetic acid, trifluoroacetic acid, and the like can be given as preferable examples, with water, methanol, N,N-dimethylacetoamide, acetonitrile, and dimethylsulfoxide being more preferable, and water and methanol being particularly preferable.

These organic solvents may be used either individually or in combination of two or more.

If necessary, the organic solvent may be used together with water. In this case, the amount of the organic solvent used is usually 5 parts by weight or more, preferably 10 parts by weight or more, and particularly preferably 20-90 parts by weight, for 100 parts by weight of the total amount of the organic solvent and water. The amount of the reaction solvent used is usually 5-100 parts by weight, preferably 10-100 parts by weight, and particularly preferably 20-50 parts by weight for 100 parts by weight of the sulfinate (1b).

The reaction is carried out at a temperature of usually 0-100° C., preferably 5-60° C., and particularly preferably 5-40° C. for usually 0.5-72 hours, and preferably 2-24 hours.

The ion exchange reaction of the sulfonate (1c) may be conducted, for example, using the method described in J. Photopolym. Sci. Tech., p. 571-576 (1998), a method of ion-exchange chromatography, or the methods used in the later-described Synthesis Examples.

As examples of the monovalent anion for $Z^-$ in the reaction formula (1), $F^-$, $Cl^-$, $Br^-$, $I^-$, perchlorate, hydrogen sulfate, dihydrogen phosphate, tetrafluoroborate, aliphatic sulfonate, aromatic sulfonate, trifluoromethane sulfonate, fluorosulfonate, hexafluorophosphate, hexachloroantimonate, and the like can be given, with $Cl^-$, $Br^-$, hydrogen sulfate, tetrafluoroborate, and aliphatic sulfonate being preferable, and $Cl^-$, $Br^-$, and hydrogen sulfate being particularly preferable.

The molar ratio of the counter-ion exchange precursor to the sulfonate (1c) is usually 0.1-10.0, preferably 0.3-4.0, and particularly preferably 0.7-2.0.

This reaction is usually carried out in a reaction solvent.

As the reaction solvent, water, organic solvents such as lower alcohols, tetrahydrofuran, N,N-dimethylformamide, N,N-dimethylacetoamide, acetonitrile, dimethylsulfoxide, and the like can be given as preferable examples, with water, methanol, N,N-dimethylacetoamide, acetonitrile, and dimethylsulfoxide being more preferable, and water being particularly preferable.

These organic solvents may be used either individually or in combination of two or more.

If necessary, the organic solvent may be used together with water. In this case, the amount of the organic solvent used is usually 5 parts by weight or more, preferably 10 parts by weight or more, and particularly preferably 20-90 parts by weight, for 100 parts by weight of the total amount of the organic solvent and water. The amount of the reaction solvent used is usually 5-100 parts by weight, preferably 10-100 parts by weight, and particularly preferably 20-50 parts by weight for 100 parts by weight of the counter-ion exchange precursor.

The reaction is usually carried out at a temperature of 0-80° C. and preferably 5-30° C. for 10 minutes to 6 hours and preferably for 30 minutes to 2 hours.

The onium sulfonate compound (1) obtained in this manner can also be purified by extraction using an organic solvent.

As examples of the organic solvent used for purification, esters such as ethyl acetate and n-butyl acetate, ethers such as diethyl ether, and alkyl halides such as methylene chloride and chloroform can be given, with organic solvents that do not mix with water being preferable.

These organic solvents may be used either individually or in combination of two or more.

The precursor (1a) can be produced by, for example, first preparing a norbornene derivative (1a-1) by a Diels Alder reaction of a corresponding α,β-unsaturated aldehyde such as acrolein with a corresponding cyclopentadiene compound according to the following reaction formula (2) or preparing a norbornene derivative (1a-2) by a Diels Alder reaction of a corresponding cyclopentadiene compound with the norbornene derivative (1a-1) according to the reaction formula (2) according to the following formula (3), optionally obtaining a norbornene derivative having three or more norbornene rings (1a-3) by repeating the reaction of the formula (3), causing these norbornene derivatives to contact with hydrogen gas in a reaction solvent in the presence of a hydrogenation catalyst such as palladium-carbon to obtain a norbornene derivative (1a-4) according to the reaction formula (4), subjecting the norbornene derivative (1a-4) to a Wittig reaction using dibromodifluoromethane and triphenylphosphine in a reaction solvent to obtain an olefin compound (1a-5) according to the following reaction formula (5) (refer to WO 02/42845 A2), and adding a hydrogen halide represented by HZ other than hydrogen fluoride in a reaction solvent to obtain the target precursor (1a) according to the following reaction formula (6).

Reaction Formula [2]

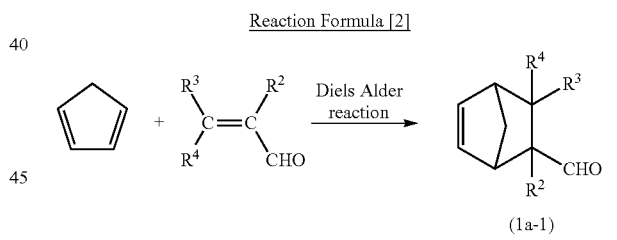

(1a-1)

Reaction Formula [3]

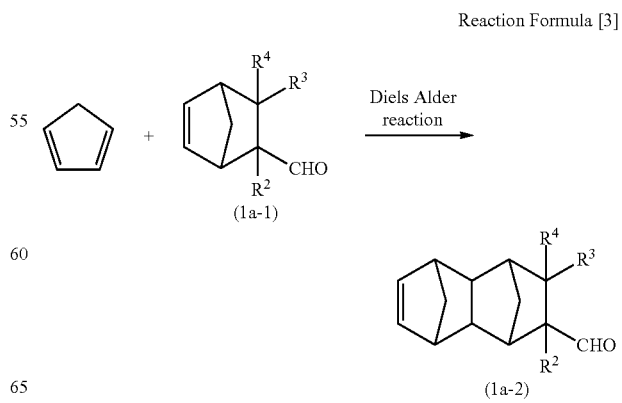

(1a-1)

(1a-2)

Reaction Formula [4]

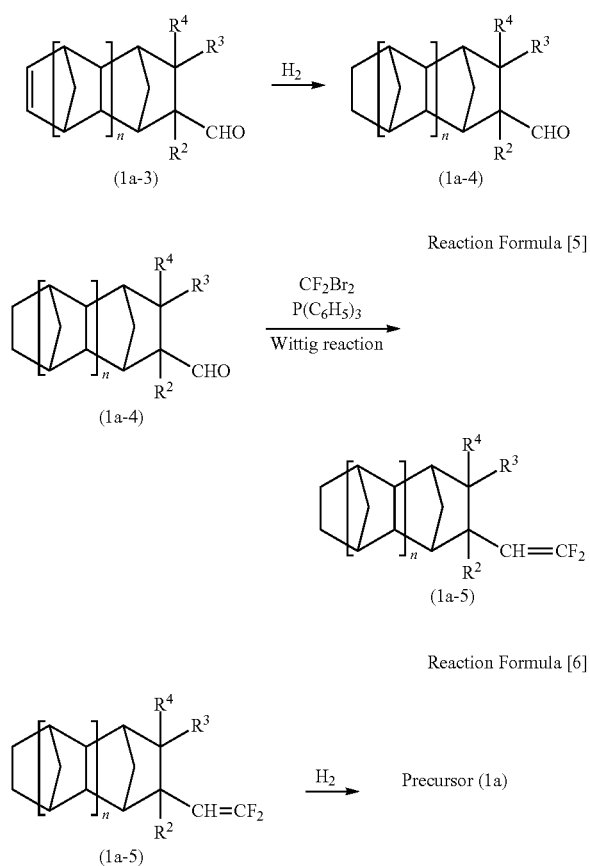

Reaction Formula [5]

Reaction Formula [6]

(Description of the substituent bonded to the carbon atoms constituting the norbornene ring is omitted.)

The onium sulfonate compound (1) can also be produced by the method disclosed in, for example, WO 02/42845 A2.

Specifically, as shown by the following reaction formula (7), the olefin compound (1a-5) is caused to react with sodium hydrogensulfite in a reaction solvent in the presence of a radical initiator such as benzoyl peroxide to produce a sulfonate (1c). The sulfonate (1c) is then ion-exchanged by a counter-ion exchange precursor $M^+Z^-$.

Reaction Formula [7]

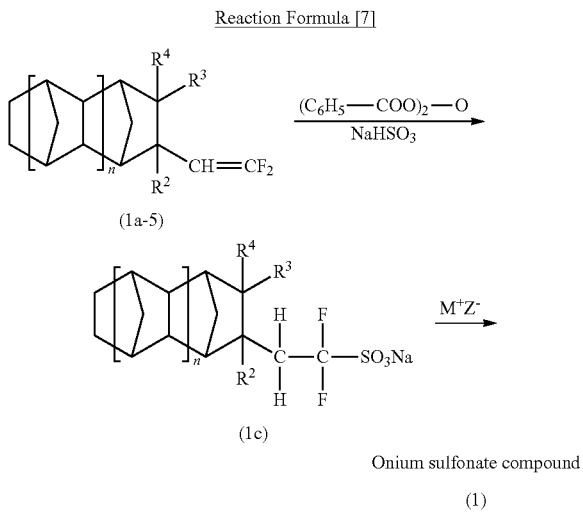

Onium sulfonate compound
(1)

(Description of the substituent bonded to the carbon atoms constituting the norbornene ring is omitted.)

The process of manufacturing the N-sulfonyloxyimide compound (2) will now be described in detail.

The N-sulfonyloxyimide compound (2) can be manufactured using the sulfinate (1b) or sulfonate (1c) shown in the reaction formula (1).

Specifically, as shown in the following reaction formula (8), the sulfinate (1b) is caused to react with a halogenation agent such as chlorine gas in a reaction solvent to obtain a sulfonylhalide compound (2a). The sulfonylhalide compound (2a) is caused to react with the N-hydroxyimide compound in a reaction solvent in the presence of a base catalyst to obtain the N-sulfonyloxyimide compound (2).

Reaction Formula [8]

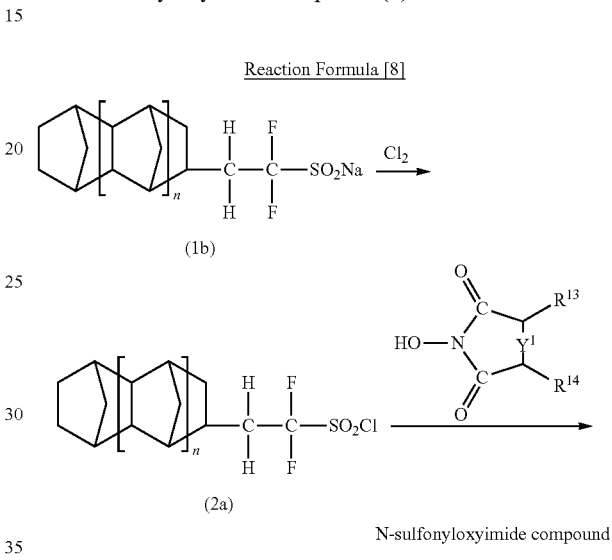

N-sulfonyloxyimide compound
(2)

(Description of the substituent bonded to the carbon atoms constituting the norbornene ring is omitted.)

The reaction of the sulfinate (1b) and the halogenating agent may be conducted, for example, using the method described in, for example, Inorganic Chemistry, Vol. 32, p. 5007-5010 (1993) or the method used in the later-described Synthesis Example 4.

As a method for adding the halogenating agent, for example, a method of blowing the halogenating agent into the reaction solution when the agent is a gas such as chlorine gas is used. When the halogenating agent is a liquid or solid, a method of charging the halogenating agent as is to the reaction solution or a method of dissolving the agent in the later described reaction solvent and adding the solution dropwise can be employed.

The halogenating agent is usually used in an amount excessive to the amount of the sulfinate (1b).

This reaction is usually carried out in a reaction solvent.

As the reaction solvent, water, organic solvents such as tetrahydrofuran, N,N-dimethylformamide, N,N-dimethylacetoamide, acetonitrile, dimethylsulfoxide, and the like can be given as preferable examples, with water, and organic solvents such as methanol, N,N-dimethylacetoamide, acetonitrile, and dimethylsulfoxide being more preferable, and water being particularly preferable.

These organic solvents may be used either individually or in combination of two or more.

If necessary, the organic solvent may be used together with water. In this case, the amount of the organic solvent used is usually 5 parts by weight or more, preferably 10 parts by weight or more, and particularly preferably 20-90 parts by weight, for 100 parts by weight of the total amount of the organic solvent and water.

The amount of the reaction solvent used is usually 5-100 parts by weight, preferably 10-100 parts by weight, and particularly preferably 20-50 parts by weight for 100 parts by weight of the sulfinate (1b).

These compounds will now be explained.

As examples of the sulfone compound, β-ketosulfone, β-sulfonylsulfone, and α-diazo compounds of these compounds can be given.

As specific examples of the sulfone compound, compounds of the following formulas (3-1) and (3-2) can be given.

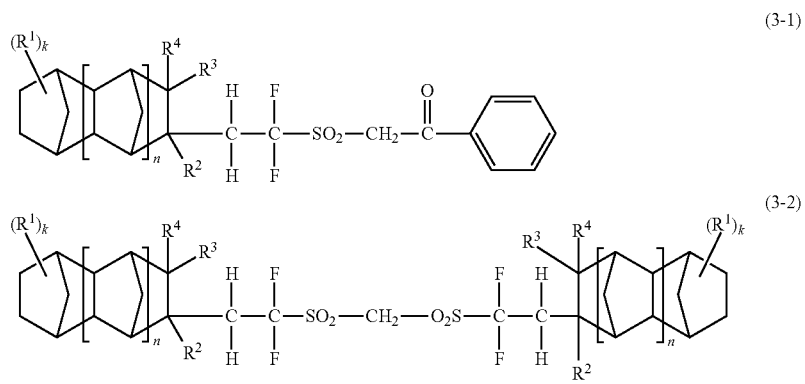

The reaction is carried out at a temperature of usually 0-100° C., preferably 5-60° C., and particularly preferably 5-40° C. for usually 5 minutes to 12 hours and preferably 10 minutes to 5 hours.

In the reaction of the sulfonyl halide compound (2a) with the N-hydroxyimide compound, the molar ratio of the N-hydroxyimide compound to the sulfonyl halide compound (2a) is usually 0.1-10.0, preferably 0.3-5.0, and particularly preferably 0.5-2.0.

This reaction is usually carried out in a reaction solvent.

As the reaction solvent, for example, organic solvents such as acetonitrile, dimethylformamide, tetrahydrofuran, dimethylsulfoxide, methylene chloride, methylene bromide, and chloroform can be given as preferable examples, with acetonitrile, tetrahydrofuran, methylene chloride, and the like being particularly preferable.

These organic solvents may be used either individually or in combination of two or more.

The amount of the reaction solvent used is usually 5-100 parts by weight, preferably 10-100 parts by weight, and particularly preferably 20-50 parts by weight for 100 parts by weight of the sulfonyl halide compound (2a).

As the above-mentioned basic catalyst, triethylamine, pyridine, N,N-di-i-propyl-ethylamine, 2,6-lutidine, N,N-diethyl aniline, 4-dimethyl aminopyridine, diazabicycloundecene, and the like can be given as preferable examples, with triethylamine, 4-dimethylaminopyridine, and the like being even more preferable.

These basic catalysts may be used either individually or in combination of two or more.

The molar ratio of the basic catalyst to the sulfonylhalide compound (2a) is usually 1.0-10.0, preferably 1.5-5.0, and more preferably 1.5-3.0.

The reaction is usually carried out at a temperature of 0-80° C. and preferably 5-30° C. for 5 minutes to 6 hours and preferably for 10 minutes to 2 hours.

As examples of an acid generator (I) other than the onium sulfonate compound (1) and N-sulfonyloxyimide compound (2), a sulfone compound, sulfonate compound, disulfonyl diazomethane compound, disufonylmethane compound, oxime sulfonate compound, hydrazine sulfonate compound, and the like can be given.

wherein $R^1$, $R^2$, $R^3$, $R^4$, k, and n are the same as defined for formula (I), and two or more $R^1$, $R^2$, $R^3$, $R^4$, k, and n groups, if present, may be either the same or different.

As examples of the sulfonate compound, alkyl sulfonate, haloalkyl sulfonate, aryl sulfonate, and imino sulfonate can be given.

As specific examples of the sulfonate compound, the compound of the following formula (4) can be given.

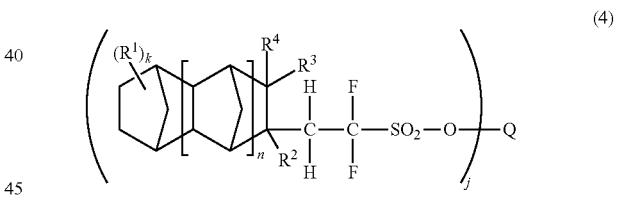

wherein $R^1$, $R^2$, $R^3$, $R^4$, k, and n are the same as defined for formula (I), two or more $R^1$, $R^2$, $R^3$, $R^4$, k, and n groups, if present, may be either the same or different, Q is a j-valent organic residue originating from pyrogallol, α-methylol benzoin, and the like, and j is an integer from 1-3.

As an example of a disulfonyldiazomethane compound, a compound shown by the following formula (5) can be given:

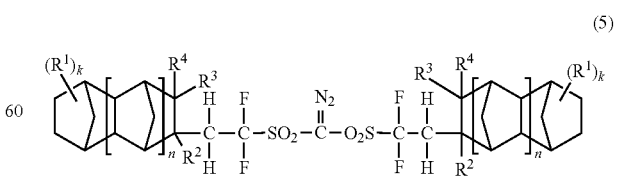

wherein $R^1$, $R^2$, $R^3$, $R^4$, k, and n are the same as defined for formula (I), and two or more $R^1$, $R^2$, $R^3$, $R^4$, k, and n groups, if present, may be either the same or different.

As an example of a disulfonylmethane compound, a compound shown by the following formula (6) can be given:

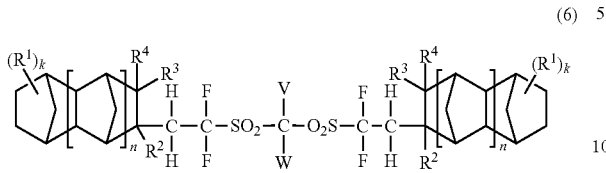
(6)

wherein $R^1$, $R^2$, $R^3$, $R^4$, k, and n are the same as defined for formula (I), two or more $R^1$, $R^2$, $R^3$, $R^4$, k, and n groups, if present, may be the same or different, V and W individually represent an aryl group, hydrogen atom, linear or branched monovalent aliphatic hydrocarbon group, or monovalent organic group having a hetero atom, wherein at least one of V and W is an aryl group, V and W combine to form a monocyclic or polycyclic structure having at least one unsaturated bond, or V and W combine to form a group of the following formula (7).

(7)

wherein V' and W' individually represent a hydrogen atom, halogen atom, alkyl group, cycloalkyl group, aryl group, or aralkyl group, or V' and W' each bond to the same or different carbon atoms to form a monocyclic carbon structure, and a is an integer from 2-10.

As examples of the oxime sulfonate compound, compounds of the following formula (8-1) or (8-2), and the like can be given:

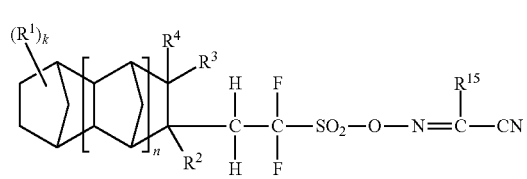
(8-1)

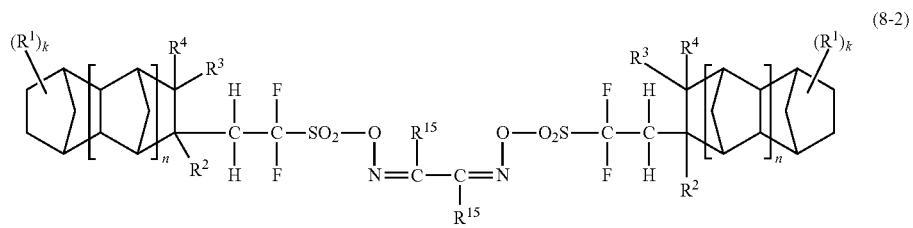
(8-2)

wherein $R^1$, $R^2$, $R^3$, $R^4$, k, and n are the same as defined for formula (I), two or more $R^1$, $R^2$, $R^3$, $R^4$, k, and n groups, if present, may be either the same or different, $R^{15}$ represents a monovalent organic group, and two or more $R^{15}$ groups, if present, may be either the same or different.

As examples of the hydrazine sulfonate compound, compounds of the following formula (9-1) or (9-2), and the like can be given:

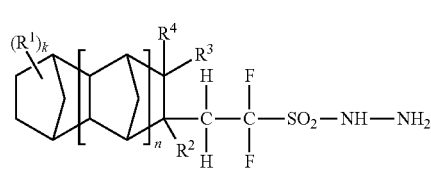
(9-1)

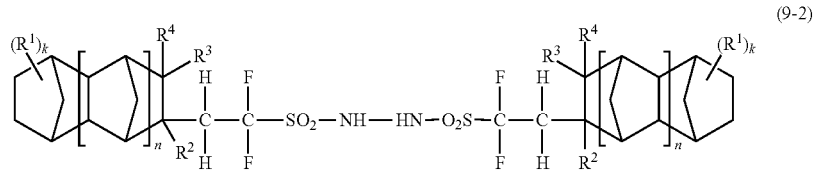
(9-2)

wherein $R^1$, $R^2$, $R^3$, $R^4$, k, and n are the same as defined for formula (I), two or more $R^1$, $R^2$, $R^3$, $R^4$, k, and n groups, if present, may be either the same or different.

Sulfonic Acid (I-a)

The sulfonic acid (I-a) is produced when the acid generator (I) is exposed or heated and is used as an acid catalyst in the formation of a resist pattern using the later-described positive-tone radiation sensitive resin composition and negative-tone radiation sensitive resin composition.

Due to the presence of a strong fluorine-containing electron drawing group in the α-position of the sulfonic acid group in the structure (I), the sulfonic acid (I-a) is highly acidic, is difficult to sublime during photolithography processing due to a high boiling point, and has a moderately short acid diffusion length in the resist film. In addition, since the amount of fluorine is less than in the higher perfluoroalkanesulfonic acid, combustibility is comparatively high and accumulation in the human body is low.

In addition to being used as a component for forming a lower layer or upper layer antireflection film in the formation of a resist pattern, the sulfonic acid (I-a) can also be used as a raw material or intermediate in the production of various related sulfonate derivatives.

Sulfonyl Halide Compound (I-b)

In addition to being very useful as a raw material or intermediate in the production of N-sulfonyloxyimide compound (2), the sulfonyl halide compound (I-b) can also be used as a raw material or intermediate in the production of related derivatives.

Positive-Tone Radiation Sensitive Resin Composition and Negative-Tone Radiation Sensitive Resin Composition Component (A)

The component (A) of the positive-tone radiation sensitive resin composition and negative-tone radiation sensitive resin composition of the present invention is a photoacid generator comprising the acid generator (I) as an essential component.

The acid generator (I) can be used either individually or in combination of two or more in the positive-tone radiation sensitive resin composition and negative-tone radiation sensitive resin composition of the present invention.

Although the amount of acid generator (I) used in the positive-tone radiation sensitive resin composition and negative-tone radiation sensitive resin composition of the present invention varies according to the types of the acid generator (I) and the following other acid generators used together, that amount is usually 0.1-20 parts by weight, preferably 0.1-15 parts by weight, and more preferably 0.2-12 parts by weight for 100 parts by weight of the acid-dissociable group-containing resin or alkali-soluble resin. If the amount of acid generator (I) is less than 0.1 part by weight, it may be difficult for the resin composition to sufficiently exhibit the target effect of the present invention. If the amount exceeds 20 parts by weight, transparency, pattern profile, heat resistance, and the like may be impaired.

One or more photoacid generators other than the acid generator (I) (hereinafter referred to as "other acid generators") can be used in combinations in the positive-tone radiation sensitive resin composition and negative-tone radiation sensitive resin composition of the present invention.

As examples of the other acid generators, onium salt compounds, sulfone compounds, sulfonate compounds, sulfonimide compounds, diazomethane compounds, disulfonylmethane compounds, oxime sulfonate compound, hydrazine sulfonate compound, and the like can be given. As examples of the onium salt compound, iodonium salts, sulfonium salts (including tetrahydrothiophenium salts), phosphonium salts, diazonium salts, ammonium salts, pyridinium salts, and the like can be given.

As examples of the sulfone compound, β-ketosulfone, β-sulfonylsulfone, and α-diazo compounds of these compounds can be given.

As examples of the sulfonate compound, alkyl sulfonate, haloalkyl sulfonate, aryl sulfonate, and imino sulfonate can be given.

As an example of the sulfonimide compound, a compound of the following formula (10), and the like can be given:

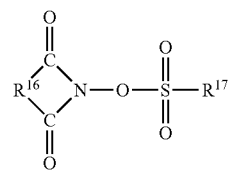

(10)

wherein $R^{16}$ is a divalent organic group and $R^{17}$ is a monovalent organic group.

As examples of $R^{16}$ in the formula (10), a methylene group, linear or branched alkylene group having 2-20 carbon atoms, aralkylene group having 2-20 carbon atoms, difluoromethylene group, linear or branched perfluoroalkylene group having 2-20 carbon atoms, cyclohexylene group, phenylene group, divalent group possessing a norbornene skeleton, or a group wherein these groups are substituted with an aryl group having six or more carbon atoms or an alkoxyl group having one or more carbon atoms can be given.

As examples of $R^{17}$, a linear or branched alkyl group having 1-10 carbon atoms, linear or branched perfluoroalkyl group having 1-10 carbon atoms, perfluorocycloalkyl group having 3-10 carbon atoms, monovalent hydrocarbon group possessing a bicyclo ring having 7-15 carbon atoms, and an aryl group having 6-12 carbon atoms, can be given.

As an example of the diazomethane compound, a compound of the following formula (11), and the like can be given:

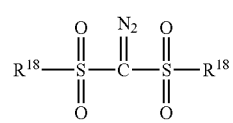

(11)

wherein $R^{18}$ individually represents a monovalent group such as a linear or branched alkyl group, cycloalkyl group, aryl group, halogenated alkyl group, halogenated cycloalkyl group, and halogenated aryl group.

As an example of the disulfonylmethane compound, a compound of the following formula (12) can be given:

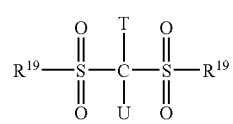

(12)

wherein $R^{19}$ individually represents a linear or branched monovalent aliphatic hydrocarbon group, cycloalkyl group, aryl group, aralkyl group, or other monovalent organic group having a hetero atom, T and U individually represent an aryl group, hydrogen atom, linear or branched monovalent aliphatic hydrocarbon group, cycloalkyl group, aralkyl group, or other monovalent organic group having a hetero atom, provided that at least one of T and U represents an aryl group, or T and U bond to form a monocyclic or polycyclic ring having at least one unsaturated bond, or T and U bond to form a group shown by the following formula (13);

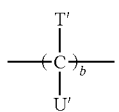
(13)

wherein the T' and U' groups individually represent a hydrogen atom, halogen atom, linear or branched alkyl group, cycloalkyl group, aryl group, or aralkyl group, or T' and U', bonded to the same or different carbon atoms, bond to each other to form a monocyclic carbon structure, and b is an integer from 2 to 10.

As examples of the oxime sulfonate compound, compounds of the following formula (14-1) or (14-2) can be given:

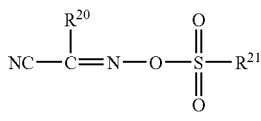
(14-1)

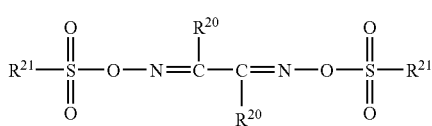
(14-2)

wherein $R^{20}$ and $R^{21}$ individually represent a monovalent organic group, and two or more $R^{20}$ and $R^{21}$ groups, if present, may be the same or different.

As specific examples of $R^{20}$ in the formulas (14-1) and (14-2), a methyl group, ethyl group, n-propyl group, phenyl group, and p-tolyl group can be given. As specific examples of $R^{21}$, a phenyl group, p-tolyl group, and 1-naphthyl group can be given.

As examples of the hydrazine sulfonate compound, compounds of the following formula (15-1) or (15-2) can be given:

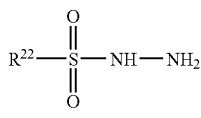
(15-1)

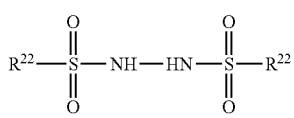
(15-2)

wherein $R^{22}$ is a monovalent organic group and two or more $R^{22}$ groups, if present, may be the same or different.

As specific examples of $R^{22}$ in the formulas (15-1) and (15-2), a methyl group, ethyl group, n-propyl group, phenyl group, p-tolyl group, trifluoromethyl group, and nonafluoro-n-butyl group can be given.

Of the other acid generators, one or more acid generators selected from the group consisting of an onium salt compound, sulfonimide compound, and diazomethane compound are preferable.

As examples of particularly preferable other acid generators, diphenyliodonium trifluoromethanesulfonate, diphenyliodonium nonafluoro-n-butanesulfonate, diphenyliodonium p-toluenesulfonate, diphenyliodonium 10-camphorsulfonate, diphenyliodonium 2-trifluoromethylbenzenesulfonate, diphenyliodonium 4-trifluoromethylbenzenesulfonate, diphenyliodonium 2,4-difluorobenzenesulfonate, diphenyliodonium 1,1,2,2-tetrafluoro-2-(norbornan-2-yl)ethanesulfonate, diphenyliodonium 2-(5-t-butoxycarbonyloxybicyclo[2.2.1]heptan-2-yl)-1,1,2,2-tetrafluoroethanesulfonate, diphenyliodonium 2-(6-t-butoxycarbonyloxybicyclo[2.2.1]heptan-2-yl)-1,1,2,2-tetrafluoroethanesulfonate, bis(4-t-butylphenyl)iodonium trifluoromethane sulfonate, bis(4-t-butylphenyl)iodonium nonafluoro-n-butanesulfonate, bis(4-t-butylphenyl)iodonium p-toluenesulfonate, bis(4-t-butylphenyl)iodonium 10-camphorsulfonate, bis(4-t-butylphenyl)iodonium 2-trifluoromethylbenzenesulfonate, bis(4-t-butylphenyl)iodonium 4-trifluoromethylbenzenesulfonate, bis(4-t-butylphenyl)iodonium 2,4-difluorobenzenesulfonate, bis(4-t-butylphenyl)iodonium 1,1,2,2-tetrafluoro-2-(norbornan-2-yl)ethanesulfonate, triphenylsulfonium trifluoromethanesulfonate, triphenylsulfonium nonafluoro-n-butanesulfonate, triphenylsulfonium p-toluenesulfonate, triphenylsulfonium 10-camphorsulfonate, triphenylsulfonium 2-trifluoromethylbenzenesulfonate, triphenylsulfonium 4-trifluoromethylbenzenesulfonate, triphenylsulfonium 2,4-difluorobenzenesulfonate, triphenylsulfonium 1,1,2,2-tetrafluoro-2-(norbornan-2-yl)ethanesulfonate, triphenylsulfonium 2-(5-t-butoxycarbonyloxybicyclo[2.2.1]heptan-2-yl)-1,1,2,2-tetrafluoroethanesulfonate, triphenylsulfonium 2-(5-t-butoxycarbonyloxybicyclo[2.2.1]heptan-2-yl)-1,1,2,2-tetrafluoroethanesulfonate, triphenylsulfonium 2-(5-pivaloyloxybicyclo[2.2.1]heptan-2-yl)-1,1,2,2-tetrafluoroethanesulfonate, triphenylsulfonium 2-(6-pivaloyloxybicyclo[2.2.1]heptan-2-yl)-1,1,2,2-tetrafluoroethanesulfonate, triphenylsulfonium 2-(5-hydroxybicyclo[2.2.1]heptan-2-yl)-1,1,2,2-tetrafluoroethanesulfonate, triphenylsulfonium 2-(6-hydroxybicyclo[2.2.1]heptan-2-yl)-1,1,2,2-tetrafluoroethanesulfonate, triphenylsulfonium 2-(5-methanesulfonyloxybicyclo[2.2.1]heptan-2-yl)-1,1,2,2-tetrafluoroethanesulfonate, triphenyl sulfonium 2-(6-methanesulfonyloxybicyclo[2.2.1]heptan-2-yl)-1,1,2,2-tetrafluoroethanesulfonate, triphenylsulfonium 2-(5-i-propanesulfonyloxybicyclo[2.2.1]heptan-2-yl)-1,1,2,2-tetrafluoroethanesulfonate, triphenylsulfonium 2-(6-i-propanesulfonyloxybicyclo[2.2.1]heptan-2-yl)-1,1,2,2-tetrafluoroethanesulfonate, triphenylsulfonium 2-(5-n-hexanesulfonyloxybicyclo[2.2.1]heptan-2-yl)-1,1,2,2-tetrafluoroethanesulfonate, triphenylsulfonium 2-(6-n-hexanesulfonyloxybicyclo[2.2.1]heptan-2-yl)-1,1,2,2-tetrafluoroethanesulfonate, triphenylsulfonium 2-(5-oxobicyclo[2.2.1]heptan-2-yl)-1,1,2,2-tetrafluoroethanesulfonate, triphenylsulfonium 2-(6-oxobicyclo[2.2.1]heptan-2-yl)-1,1,2,2-tetrafluoroethanesulfonate, 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, 1-(4-n-butoxynaphthalen-1-yl)tetrahydrothiophenium 1,1,2,2-tetrafluoro-2-(norbornan-2-yl)ethanesulfonate, 1-(4-n-butoxynaphthalen-1-yl)tetrahydrothiophenium 2-(5-t-butoxycarbonyloxybicyclo[2.2.1]heptan-2-yl)-1,1,2,2-tetrafluoroethanesulfonate, 1-(4- n-butoxynaphthalen-1-yl)tetrahydrothiophenium 2-(6-t-butoxycarbonyloxybicyclo[2.2.1]heptan-2-yl)-1,1,2,2-tetrafluoroethanesulfonate, N-(trifluoromethanesulfonyloxy) succinimide, N-(10-camphorsulfonyloxy)succinimide, N-{ (5-methyl-5-carboxymethanebicyclo[2,2,1]heptan-2-yl) sulfonyloxy}succinimide, N-(trifluoromethanesulfonyloxy) bicyclo[2.2.1]hept-5-ene-2,3-dicarboxyimide, N-(nonafluoro-n-butanesulfonyloxy)bicyclo[2.2.1]hept-5-ene-2,3-dicarboxyimide, N-[1,1,2,2-tetrafluoro-2-(norbornan-2-yl)ethanesulfonyloxy]bicyclo[2.2.1]hept-5-ene-2,3-dicarboxyimide, N-(10-camphorsulfonyloxy)bicyclo[2.2.1] hept-5-ene-2,3-dicarboxyimide, N-[2-(5-oxobicyclo[2.2.1] heptan-2-yl)-1,1,2,2-tetrafluoroethanesulfonyloxy]bicyclo [2.2.1]hept-5-ene-2,3-dicarboxyimide, N-[2-(6-oxobicyclo [2.2.1]heptan-2-yl)-1,1,2,2-tetrafluoroethanesulfonyloxy] bicyclo[2.2.1]hept-5-ene-2,3-dicarboxyimide, bis (cyclohexanesulfonyl)diazomethane, bis(t-butylsulfonyl) diazomethane, and bis(1,4-dioxaspiro[4.5]-decane-7-sulfonyl)diazomethane can be given.

The proportion of the other acid generators can be appropriately determined according to the types of each acid generator from the range of 95 parts by weight or less, preferably 90 parts by weight or less, and particularly preferably 80 parts by weight or less for 100 parts by weight of the total amount of the acid generator (I) and the other acid generators. If the proportion of the other acid generators exceeds 95 parts by weight, the desired effects of the present invention may be impaired.

Component (B)

The component (B) of the positive-tone radiation sensitive composition of the present invention is an acid-dissociable group-containing resin which is insoluble or scarcely soluble in alkali, but becomes easily soluble in alkali when the acid-dissociable group dissociates (hereinafter referred to as "acid-dissociable group-containing resin (B)").

If 50% or more of the initial film thickness of a resist film remains after development when a resist film made only from the acid-dissociable group-containing resin (B) is developed under the same alkaline development conditions employed for forming a resist pattern using a resist film formed from a radiation sensitive resin composition comprising the acid-dissociable group-containing resin (B), such a characteristic of the acid-dissociable group-containing resin (B) is referred to as "insoluble or scarcely soluble in alkali" in the present invention.

The acid-dissociable group of the acid-dissociable group-containing resin (B) refers to a group in which the hydrogen atom in an acid-functional group such as a phenolic hydroxyl group, carboxyl group, and sulfonic group is substituted and is dissociable in the presence of an acid.

As examples of such an acid-dissociable group, a substituted methyl group, 1-substituted ethyl group, 1-substituted n-propyl group, 1-branched alkyl group, alkoxycarbonyl group, acyl group, cyclic acid-decomposable group, and the like can be given.

As examples of the substituted methyl group, a methoxymethyl group, methylthiomethyl group, ethoxymethyl group, ethylthiomethyl group, (2-methoxyethoxy)methyl group, benzyloxymethyl group, benzylthiomethyl group, phenacyl group, 4-bromophenacyl group, 4-methoxyphenacyl group, 4-methylthiophenacyl group, α-methylphenacyl group, cyclopropylmethyl group, benzyl group, diphenylmethyl group, triphenylmethyl group, 4-bromobenzyl group, 4-nitrobenzyl group, 4-methoxybenzyl group, 4-methylthiobenzyl group, 4-ethoxybenzyl group, 4-ethylthiobenzyl group, piperonyl group, methoxycarbonylmethyl group, ethoxycarbonylmethyl group, n-propoxycarbonylmethyl group, i-propoxycarbonylmethyl group, n-butoxycarbonylmethyl group, t-butoxycarbonylmethyl group, and the like can be given.

As examples of the 1-substituted ethyl group, a 1-methoxyethyl group, 1-methylthioethyl group, 1,1-dimethoxyethyl group, 1-ethoxyethyl group, 1-ethylthioethyl group, 1,1-diethoxyethyl group, 1-phenoxyethyl group, 1-phenylthioethyl group, 1,1-diphenoxyethyl group, 1-benzyloxyethyl group, 1-benzylthioethyl group, 1-cyclopropyloxyethyl group, 1-cyclohexyloxyethyl group, 1-phenylethyl group, 1,1-diphenylethyl group, 1-methoxycarbonylethyl group, 1-ethoxycarbonylethyl group, 1-n-propoxycarbonylethyl group, 1-i-propoxycarbonylethyl group, 1-n-butoxycarbonylethyl group, and 1-t-butoxycarbonylethyl group can be given.

As examples of the 1-substituted n-propyl group, a 1-methoxy-n-propyl group and 1-ethoxy-n-propyl group can be given.

As examples of the 1-branched alkyl group, an i-propyl group, 1-methylpropyl group, t-butyl group, 1,1-dimethylpropyl group, 1-methylbutyl group, and 1,1-dimethylbutyl group can be given.

As examples of the alkoxycarbonyl group, a methoxycarbonyl group, ethoxycarbonyl group, i-propoxycarbonyl group, t-butoxycarbonyl group, and the like can be given.

As examples of the acyl group, an acetyl group, propionyl group, butyryl group, heptanoyl group, hexanoyl group, valeryl group, pivaloyl group, isovaleryl group, lauryloyl group, myristoyl group, palmitoyl group, stearoyl group, oxalyl group, malonyl group, sccucinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydroatropoyl group, atropoyl group, cinnamoyl group, furoyl group, thenoyl group, nicotinoyl group, isonicotinoyl group, p-toluenesulfonyl group, and mesyl group can be given.

As examples of the cyclic acid-decomposable group, a cyclopropyl group, cyclopentyl group, cyclohexyl group, cyclohexenyl group, 4-methoxycyclohexyl group, tetrahydropyranyl group, tetrahydrofuranyl group, tetrahydrothiopyranyl group, tetrahydrothiofuranyl group, 3-bromotetrahydropyranyl group, 4-methoxytetrahydropyranyl group, 4-methoxytetrahydrothiopyranyl group, and 3-tetrahydrothiophene-1,1-dioxide group can be given.

Of these acid-dissociable groups, a benzyl group, t-butoxycarbonylmethyl group, 1-methoxyethyl group, 1-ethoxyethyl group, 1-cyclohexyloxyethyl group, 1-ethoxy-n-propyl group, t-butyl group, 1,1-dimethylpropyl group, t-butoxycarbonyl group, tetrahydropyranyl group, tetrahydrofuranyl group, tetrahydrothiopyranyl group, tetrahydrothiofuranyl group, and the like are preferable.

The acid-dissociable group-containing resin (B) may contain one or more acid-dissociable groups.

The amount of the acid-dissociable group introduced into the acid-dissociable group-containing resin (B) (the amount of the number of acid-dissociable groups in the total number of acidic functional groups and acid-dissociable groups in the acid-dissociable group-containing resin (B)) is preferably 5-100%, and still more preferably 10-100%, although the amount varies depending on the type of acid-dissociable group and the type of resin into which the acid-dissociable group is introduced.

Various types of structure for the acid-dissociable group-containing resin (B) may be used without any restrictions as long as the above properties can be obtained. Preferable structures include a resin in which part or all of the hydrogen atoms in the phenolic hydroxyl groups of a poly(4-hydroxystyrene) are replaced by acid-dissociable groups, a copolymer of 4-hydroxystyrene and/or 4-hydroxy-α-methylstyrene and (meth)acrylic acid in which part or all of the hydrogen atoms in the phenolic hydroxyl groups and/or carboxyl groups are replaced by acid-dissociable groups, and the like.

Also, the structure of the acid-dissociable group-containing resin (B) can be appropriately determined according to the type of radiation employed.

As an acid-dissociable group-containing resin (B) particularly preferable for a positive-tone radiation sensitive resin composition using a KrF excimer laser, an alkali-insoluble or scarcely alkali-soluble resin having a recurring unit of the following formula (16) (hereinafter referred to as "recurring unit (16)") and a recurring unit in which the phenolic hydroxyl group in the recurring unit (16) is protected by an acid-dissociable group can be given. This resin is hereinafter referred to as "resin (B1)". The resin (B1) may also be suitably used in positive-tone radiation sensitive resin compositions for use with other radiations such as ArF excimer laser, F$_2$ excimer laser, and electron beams.

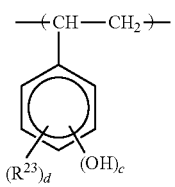

(16)

wherein R$^{23}$ individually represent a hydrogen atom or monovalent organic group, and c and d each represent an integer from 1-3.

As the recurring unit (16), units in which the non-aromatic double bond of 4-hydroxystyrene is cleaved are preferable.

The resin (B1) may further contain other recurring units.

As examples of the other recurring unit, vinyl aromatic compounds such as styrene; units obtained by cleavage of a polymerizable unsaturated bond of (meth)acrylic esters such as t-butyl(meth)acrylate, adamantyl(meth)acrylate, and 2-methyladamantyl(meth)acrylate; and the like can be given.

As a preferable example of the acid-dissociable group-containing resin (B) especially suitable for a positive-tone radiation sensitive resin composition using an ArF excimer laser, an alkali soluble or scarcely soluble resin having at least one recurring unit such as the recurring unit of the following formula (17) (hereinafter referred to as "recurring unit (17)"), and/or the recurring unit of the following formula (18) (hereinafter referred to as "recurring unit (18)"), and the recurring unit of the following formula (19) (hereinafter referred to as "recurring unit (19)") can be given. This resin is hereinafter referred to as "resin (B2)". The resin (B2) may also be suitably used in positive-tone radiation sensitive resin compositions for use with other radiations such as KrF excimer laser, F$_2$ excimer laser, and electron beams.

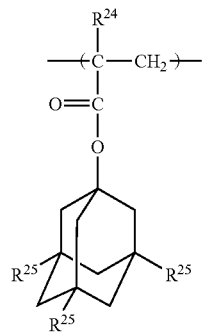

(17)

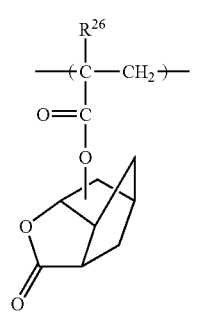

(18)

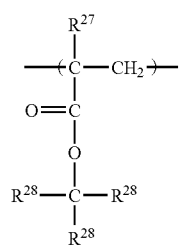

(19)

wherein R$^{24}$, R$^{26}$, and R$^{27}$ groups individually represent a hydrogen atom or methyl group and R$^{25}$ groups individually represent a hydrogen atom, hydroxyl group, cyano group, or —COOR$^{29}$, wherein R$^{29}$ represents a hydrogen atom, a linear or branched alkyl group having 1-4 carbon atoms, or a cycloalkyl group having 3-20 carbon atoms, wherein R$^{28}$ groups individually represent a monovalent alicyclic hydrocarbon group having 4-20 carbon atoms or a derivative thereof, or a linear or branched alkyl group having 1-4 carbon atoms, provided that at least one of the R$^{28}$ groups is the monovalent alicyclic hydrocarbon group having 4-20 carbon atoms or the derivative thereof, or any two of the R$^{28}$ groups form, in combination and together with the carbon atoms to which the two R$^{28}$ groups bond, a divalent alicyclic hydrocarbon group having 4-20 carbon atoms or a derivative thereof, with the remaining R$^{28}$ group being the linear or branched alkyl group having 1-4 carbon atoms or the monovalent alicyclic hydrocarbon group having 4-20 carbon atoms or the derivative thereof.

As preferable examples of the recurring unit (17), 3-hydroxyadamantan-1-yl (meth)acrylate, 3,5-dihydroxyadamantan-1-yl (meth)acrylate, 3-cyanoadamantan-1-yl (meth)acrylate, 3-carboxyadamantan-1-yl (meth)acrylate, 3,5-dicarboxyadamantan-1-yl (meth)acrylate, 3-carboxy-5-hydroxyadamantan-1-yl (meth)acrylate, 3-methoxycarbonyl-5-hydroxyadamantan-1-yl (meth)acrylate, and the like can be given.

As preferable examples of the recurring unit (19), 1-methylcyclopentyl(meth)acrylate, 1-ethylcyclopentyl(meth)acrylate, 1-methylcyclohexyl(meth)acrylate, 1-ethylcyclohexyl (meth)acrylate, 2-methyladamantan-2-yl (meth)acrylate, 2-ethyladamantan-2-yl (meth)acrylate, 2-n-propyladamantan-2-yl (meth)acrylate, 2-i-propyladamantan-2-yl (meth) acrylate, 1-(adamantan-1-yl)-1-methylethyl(meth)acrylate, and the like can be given.

The resin (B2) may further contain other recurring units.

As examples of monomers providing the other recurring units, monofunctional monomers such as (meth)acrylic esters such as 7-oxo-6-oxabicyclo[3.2.1]octan-4-yl (meth)acrylate, 2-oxotetrahydropyran-4-yl (meth)acrylate, 4-methyl-2-oxotetrahydropyran-4-yl (meth)acrylate, 5-oxotetrahydrofuran-3-yl (meth)acrylate, 2-oxotetrahydrofuran-3-yl (meth)acrylate, (5-oxotetrahydrofuran-2-yl)methyl(meth)acrylate, and (3,3-dimethyl-5-oxotetrahydrofuran-2-yl)methyl(meth) acrylate; unsaturated amide compounds such as (meth)acrylamide, N,N-dimethyl(meth)acrylamide, crotonamide, maleinamide, fumaramide, mesaconamide, citraconamide, and itaconamide; unsaturated polycarboxylic anhydrides such as maleic anhydride and itaconic anhydride; mono-functional monomers such as bicyclo[2.2.1]hept-2-ene and the derivative thereof and tetracyclo[6.2.1$^{3,6}$.0$^{2,7}$]dodec-3-ene and the derivative thereof; and polyfunctional monomers such as methylene glycol di(meth)acrylate, ethylene glycol di(meth)acrylate, 2,5-dimethyl-2,5-hexanediol di(meth) acrylate, 1,2-adamantandiol di(meth)acrylate, 1,3-adamantandiol di(meth)acrylate, 1,4-adamantandiol di(meth) acrylate, and tricyclodecane dimethylol di(meth)acrylate can be given.

As a preferable example of the acid-dissociable group-containing resin (B) especially suitable for a positive-tone radiation sensitive resin composition using an $F_2$ excimer laser, an alkali soluble or scarcely soluble polysiloxane having a structural unit of the following formula (20) (hereinafter referred to as "structural unit (20)") and/or a structural unit of the following formula (21) (hereinafter referred to as "structural unit (21)") can be given. This resin is hereinafter referred to as "resin (B3)". The resin (B3) may also be suitably used in positive-tone radiation sensitive resin compositions for use with KrF excimer laser, ArF excimer laser, and electron beams.

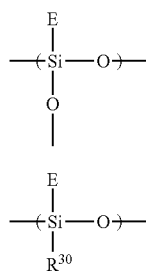

wherein E individually represents a monovalent organic group having an acid-dissociable group and $R^{30}$ represents a substituted or unsubstituted, linear, branched, or cyclic monovalent hydrocarbon group having 1-20 carbon atoms.

In the formulas (20) and (21), E is preferably a group having an acid-dissociable group in the alicyclic hydrocarbon group such as a cycloalkyl group, norbornyl group, tricyclodecanyl group, tetracyclodecanyl group, and adamantyl group, or a group having an acid-dissociable group in the halogenated aromatic hydrocarbon group.

As a particularly preferable structural unit (20) for the resin (B3), the structural units of the following formulas (20-1)-(20-4) can be given.

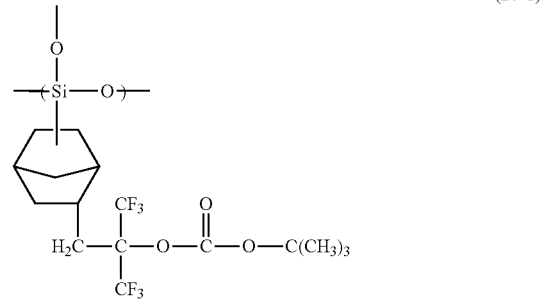

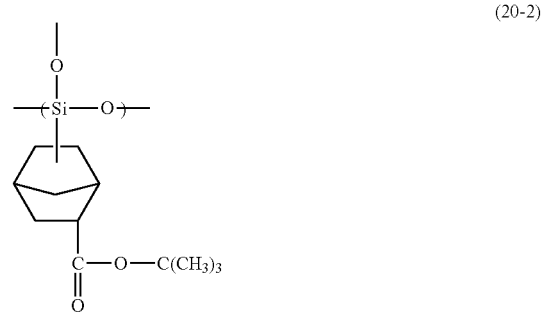

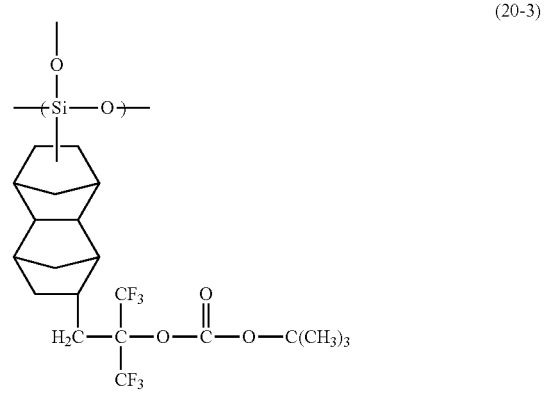

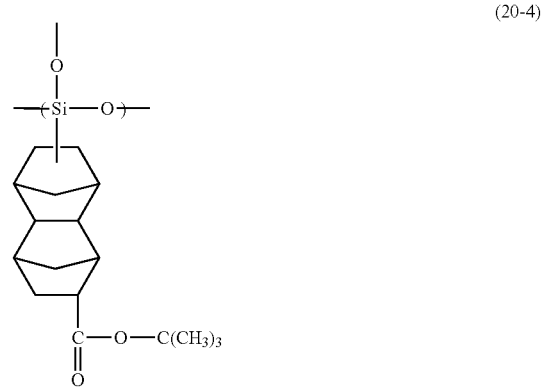

The resin (B3) may contain one or more other structural units (hereinafter referred to as "other structural units").

As examples of preferable other structural units, structural units obtained by hydrolysis-condensation of alkyl alkoxysilanes such as methyl trimethoxysilane, methyl triethoxysilane, ethyl trimethoxysilane, and ethyl triethoxysilane, and the structural units of the following formulas (22-1)-(22-4) can be given.

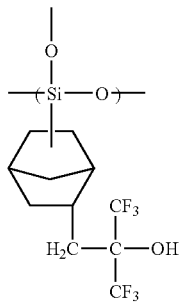

(22-1)

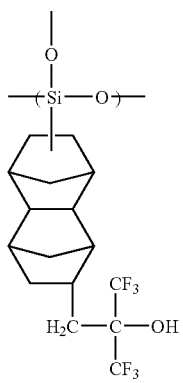

(22-2)

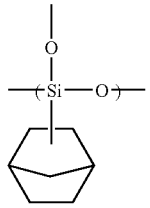

(22-3)

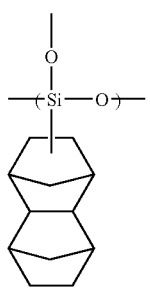

(22-4)

The resin (B-3) can be prepared by (co)polycondensation of a silane compound containing one or more acid-dissociable groups or by introducing one or more acid-dissociable groups into a previously prepared organic polysiloxane.

When (co)polycondensing the acid-dissociable group-containing silane compound, an acidic catalyst is preferably used as the catalyst, and after polycondensation of the silane compound in the presence of the acidic catalyst, a further reaction is preferably continued in the presence of a basic catalyst.

As examples of the acidic catalyst, inorganic acids such as hydrochloric acid, sulfuric acid, nitric acid, boric acid, phosphoric acid, titanium tetrachloride, zinc chloride, and aluminium chloride and organic acids such as formic acid, acetic acid, n-propionic acid, butyric acid, valeric acid, oxalic acid, malonic acid, succinic acid, maleic acid, fumaric acid, adipic acid, phthalic acid, terephthalic acid, acetic anhydride, maleic anhydride, citric acid, benzenesulfonic acid, p-toluenesulfonic acid, and methanesulfonic acid can be given.

Of these acidic catalysts, hydrochloric acid, sulfuric acid, acetic acid, oxalic acid, malonic acid, maleic acid, fumaric acid, acetic anhydride, maleic anhydride, and the like are preferable.

As examples of the basic catalyst, inorganic bases such as lithium hydroxide, sodium hydroxide, potassium hydroxide, calcium hydroxide, barium hydroxide, sodium hydrogencarbonate, potassium hydrogencarbonate, sodium carbonate, and potassium carbonate and organic bases such as triethylamine, tri-n-propylamine, tri-n-butylamine, and pyridine can be given.

When the acid-dissociable group-containing resin (B) is prepared by a reaction or reactions comprising the polymerization of a polymerizable unsaturated monomer, a branched structure may be introduced into the acid-dissociable group-containing resin by a unit derived from a polyfunctional monomer having two or more polymerizable unsaturated bonds and/or by an acetal crosslinking group. Introduction of the branched structure improves the heat resistance of the acid-dissociable group-containing resin (B).

The amount of the branched structure introduced into the acid-dissociable group-containing resin (B) is preferably 10 mol % or less of the total amount of recurring units, although such an amount varies according to the type of branched structure and the type of acid-dissociable group-containing resin into which the branched structure is introduced.

The molecular weight of the acid-dissociable group-containing resin (B) may be appropriately selected without any restrictions. The polystyrene-reduced weight molecular weight (hereinafter referred to as "Mw") of the acid-dissociable group-containing resin (B) determined by gel permeation chromatography (GPC) is usually 1,000-500,000, preferably 2,000-400,000, and still more preferably 3,000-300,000.

The Mw of the acid-dissociable group-containing resin (B) not having a branched structure is preferably 1,000-150,000, and particularly preferably 3,000-100,000. The Mw of the acid-dissociable group-containing resin (B) having a branched structure is preferably 5,000-500,000, and particularly preferably 8,000-300,000. The resist obtained from the acid-dissociable group-containing resin (B) having an Mw in the above ranges possesses excellent development characteristics.

The ratio of Mw to the polystyrene-reduced number average molecular weight (hereinafter referred to as "Mn") determined by GPC (Mw/Mn) of the acid-dissociable group-containing resin (B) can be appropriately selected without any restrictions, and is usually 1-10, preferably 1-8, and particularly preferably 1-5. The resist obtained from the acid-dissociable group-containing resin (B) having a Mw/Mn in this range possesses excellent resolution performance.

The acid-dissociable group-containing resin (B) can be used either individually or in combination of two or more in the positive-tone radiation sensitive resin composition of the present invention.

There are no restrictions to the method for manufacturing the acid-dissociable group-containing resin (B). As examples of the method for manufacturing, a method of introducing one or more acid-dissociable groups into an acidic functional group of an alkali-soluble resin which has previously been manufactured, a method of polymerizing polymerizable unsaturated monomers having an acid-dissociable group, optionally together with one or more other polymerizable unsaturated monomers, a method of polycondensing one or more polycondensation components having an acid-dissociable group, optionally together with other polymerizable unsaturated monomers, and the like can be given.

The polymerization of the polymerizable unsaturated monomers and the polymerization of the polymerizable unsaturated monomers possessing an acid-dissociable group in the manufacture of the alkali soluble resin is carried out by block polymerization, solution polymerization, precipitation polymerization, emulsion polymerization, suspension polymerization, block-suspension polymerization, or the like using an appropriate polymerization initiator or catalyst such as a radical polymerization initiator, anionic polymerization catalyst, coordinated anionic polymerization catalyst, cationic polymerization catalyst, or the like according to the type of polymerizable unsaturated monomer or reaction media.

The polycondensation of the polycondensable components having an acid-dissociable group is preferably carried out in the presence of an acidic catalyst using an aqueous medium or a mixture of water and a hydrophilic solvent.

The amount of the photoacid generator used in the positive-tone radiation sensitive resin composition of the present invention can be appropriately selected depending on the desired properties of the resist. The photoacid generator is preferably used in an amount of 0.001-70 parts by weight, more preferably 0.01-50 parts by weight, and particularly preferably 0.1-20 parts by weight for 100 parts by weight of the acid-dissociable group containing resin (B). Using the photoacid generator in an amount of 0.001 parts by weight or more prevents deterioration of the sensitivity and resolution of the resist. Also, using the acid generator in an amount of 70 parts by weight or less prevents deterioration of the applicability and pattern shape of the resist.

Component (C)

The component (C) of the negative-tone radiation sensitive composition of the present invention is an alkali-soluble resin containing at least one oxygen-containing functional group having an affinity with an alkaline developer such as a phenolic hydroxyl group, alcoholic hydroxyl group, and carboxyl group. The alkali-soluble resin is dissolved in an alkali developer.

As examples of the alkali soluble resin, an addition polymerization type resin possessing at least one recurring unit selected from the group consisting of a recurring unit of the following formula (23) (hereinafter referred to as "recurring unit (23)"), a recurring unit of the following formula (24) (hereinafter referred to as "recurring unit (24)"), and a recurring unit of the following formula (25) (hereinafter referred to as "recurring unit (25)") can be given.

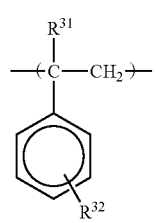

(23)

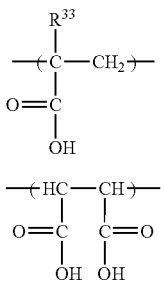

wherein $R^{31}$ and $R^{33}$ individually represent a hydrogen atom or a methyl group, $R^{32}$ represents a hydroxyl group, carboxyl group, —$R^{34}$COOH, —O$R^{34}$COOH, —OCO$R^{34}$COOH, or —COO$R^{34}$COOH, wherein $R^{34}$ individually represents —$(CH_2)_e$—, wherein e is an integer of 1-4.

Although the alkali-soluble resin may comprise only the recurring unit (23), the recurring unit (24), or the recurring unit (25), the alkali-soluble resin may comprise one or more other recurring units as long as the obtained resin is soluble in an alkaline developer.

As examples of the other recurring units, the same other recurring units given for the resin (B1) can be given.

Although the total content of the recurring unit (23), recurring unit (24), and recurring unit (25) in the alkali-soluble resin depends on the type of other recurring units contained in the resin, a content of 10-100 mol % is preferable, with 20-100 mol % being more preferable.

When the alkali-soluble resin comprises a recurring unit possessing carbon-carbon unsaturated bonds such as the recurring unit (23), the alkali-soluble resin can be used after hydrogenation. In this case, the hydrogenation degree is usually 70% or less, preferably 50% or less, and still more preferably 40% or less of the total amount of the carbon-carbon unsaturated bonds in the recurring units, and the like. If the hydrogenation degree is more than 70%, developability of the alkali-soluble resin by an alkaline developer may decrease.

As the alkali-soluble resin of the present invention, a resin containing poly(4-hydroxystyrene), 4-hydroxystyrene/4-hydroxy-α-methylstyrene copolymer, 4-hydroxystyrene/styrene copolymer, or the like as a major component is particularly preferable.

Although Mw of the alkali-soluble resin varies according to the characteristics desired for the negative-tone radiation sensitive resin composition, a usual range is 1,000-150,000, with the range of 3,000-100,000 being preferable.

The above-described alkali-soluble resins may be used either individually or in combination of two or more in the negative-tone radiation sensitive resin composition.

Component (D)

The component (D) of the negative-tone radiation sensitive resin composition of the present invention is a compound that crosslinks the alkali-soluble resin in the presence of an acid (hereinafter referred to as "crosslinking agent").

As an example of such a crosslinking agent, a compound having a functional group (hereinafter referred to as "crosslinkable functional group") which exhibits crosslinking reactivity with the alkali-soluble resin can be given.

As examples of such a crosslinkable functional group, a glycidyl ether group, glycidyl ester group, glycidyl amino group, methoxymethyl group, ethoxymethyl group, benzyloxymethyl group, acetoxymethyl group, benzoiloxy methyl group, formyl group, acetyl group, vinyl group, iso-propenyl group, (dimethylamino)methyl group, (diethylamino)methyl group, (dimethylolamino)methyl group, (diethylolamino)methyl group, and morpholinomethyl group can be given.

As examples of the crosslinking agent, a bisphenol A epoxy compound, bisphenol F epoxy compound, bisphenol S epoxy compound, novolac resin epoxy compound, resol resin epoxy compound, poly(hydroxystyrene) epoxy compound, methylol group-containing melamine compound, methylol group-containing benzoguanamine compound, methylol group-containing urea compound, methylol group-containing phenol compound, alkoxyalkyl group-containing melamine compound, alkoxyalkyl group-containing benzoguanamine compound, alkoxyalkyl group-containing urea compound, alkoxyalkyl group-containing phenol compound, carboxymethyl group-containing melamine resin, carboxymethyl group-containing benzoguanamine resin, carboxymethyl group-containing urea resin, carboxymethyl group-containing phenol resin, carboxymethyl group-containing melamine compound, carboxymethyl group-containing benzoguanamine compound, carboxymethyl group-containing urea compound, and carboxymethyl group-containing phenol compound can be given.

Of these crosslinking agents, a methylol group-containing phenol compound, methoxymethyl group-containing melamine compound, methoxymethyl group-containing phenol compound, methoxymethyl group-containing glycoluril compound, methoxymethyl group-containing urea compound, and acetoxymethyl group-containing phenol compound are preferable, with particularly preferable compounds being a methoxymethyl group-containing melamine compound (for example, hexamethoxymethylmelamine), methoxymethyl group-containing glycoluril compound, methoxymethyl group-containing urea compound, and the like. Methoxymethyl group-containing melamine compounds are commercially available under the trademarks CYMEL300, CYMEL301, CYMEL303, and CYMEL305 (manufactured by Mitsui Cyanamid Co., Ltd.), methoxymethyl group-containing glycoluril compounds are commercially available under the trademark CYMEL 1174 (manufactured by Mitsui Cyanamid Co., Ltd.) and the like; and methoxymethyl group-containing urea compounds are commercially available under the trademark MX290 (manufactured by Sanwa Chemical Co., Ltd.) and the like.

A resin provided with crosslinking characteristics by replacing a hydrogen atom of an oxygen-containing functional group in the alkali-soluble resin with the above-mentioned crosslinkable functional group can also be suitably used as the crosslinking agent. The amount of the crosslinkable functional group introduced is usually 5-60 mol %, preferably 10-50 mol %, and still more preferably 15-40 mol % of the total oxygen-containing functional groups in the alkali-soluble resin, although the specific percentage may vary depending on the types of the crosslinkable functional group and the alkali-soluble resin into which the group is introduced. The amount of crosslinkable functional group less than 5 mol % may decrease the rate of residual films and tends to induce meandering and swelling of the patterns. If the amount exceeds 60 mol %, developability of exposed areas tends to decrease.

Methoxymethyl group-containing compounds, more specifically, dimethoxymethyl urea and tetramethoxymethyl glycoluril are particularly preferable as the crosslinking agent in the present invention.

The above-described crosslinking agents may be used either individually or in combination of two or more in the negative-tone radiation sensitive resin composition.

The amount of the photoacid generator to be used in the negative-tone radiation sensitive resin composition is preferably 0.01-70 parts by weight, still more preferably 0.1-50 parts by weight, and particularly preferably 0.5-20 parts by weight for 100 parts by weight of the alkali-soluble resin. The amount of the photoacid generator less than 0.01 part by weight may impair sensitivity and resolution. If the amount exceeds 70 parts by weight, resist coating properties and pattern configuration tend to be affected.

The amount of the crosslinking agent to be used is preferably 5-95 parts by weight, still more preferably 15-85 parts by weight, and particularly preferably 20-75 parts by weight for 100 parts by weight of the alkali-soluble resin. The amount of the crosslinking agent less than 5 parts by weight may decrease the rate of residual films and tends to induce meandering and swelling of the patterns. If the amount exceeds 95 parts by weight, developability of exposed areas tends to decrease.

Other Additives

An acid diffusion controller is preferably added to the positive-tone radiation sensitive resin composition and negative-tone radiation sensitive resin composition of the present invention. The acid diffusion controller controls diffusion of an acid generated from the photoacid generator upon exposure in the resist film and prevents unfavorable chemical reactions in the unexposed region. Addition of the acid diffusion controller further improves storage stability of the resulting radiation sensitive resin composition and resolution of the resist. Moreover, addition of the acid diffusion controller prevents the line width of the resist pattern from changing due to changes in the post-exposure delay (PED) between exposure and development, whereby a radiation sensitive resin composition with remarkably superior process stability can be obtained.

As the acid diffusion controller, nitrogen-containing organic compounds of which the basicity does not change due to exposure or heat treatment during formation of a resist pattern are preferable.

As the nitrogen-containing organic compound, a compound of the following formula (26) (hereinafter called "nitrogen-containing compounds (α)"), a diamino compound having two nitrogen atoms in the molecule (hereinafter called "nitrogen-containing compounds (β)"), a polyamino compound having three or more nitrogen atoms (hereinafter called "nitrogen-containing compounds (γ)"), a compound containing an amide group, a urea compound, a heterocyclic compound containing a nitrogen atom, and the like can be given.

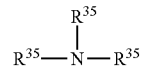

(26)

wherein $R^{35}$ individually represents a hydrogen atom, alkyl group, aryl group, or aralkyl group which may be substituted or unsubstituted.

Given as examples of the substituted or unsubstituted alkyl group represented by $R^{35}$ in the above formula (26) are groups having 1-15 carbon atoms and preferably 1-10 carbon atoms including specific examples such as a methyl group, ethyl group, n-propyl group, i-propyl group, n-butyl group, 2-methylpropyl group, 1-methylpropyl group, t-butyl group, n-pentyl group, neopentyl group, n-hexyl group, n-heptyl group, n-octyl group, n-ethylhexyl group, n-nonyl group, and n-decyl group.

Given as examples of the substituted or unsubstituted aryl group represented by $R^{35}$ are groups having 6-12 carbon atoms including specific examples such as a phenyl group, o-tolyl group, m-tolyl group, p-tolyl group, 2,3-xylyl group, 2,4-xylyl group, 2,5-xylyl group, 2,6-xylyl group, 3,4-xylyl group, 3,5-xylyl group, cumenyl group, and 1-naphthyl group.

Given as examples of the substituted or unsubstituted aralkyl group represented by $R^{35}$ are groups having 7-19 carbon atoms and preferably 7-13 carbon atoms including specific examples such as a benzyl group, α-methylbenzyl group, phenethyl group, and 1-naphthylmethyl group.

Examples of the nitrogen-containing compounds (α) include monoalkylamines such as n-hexylamine, n-heptylamine, n-octylamine, n-nonylamine, and n-decylamine; dialkylamines such as di-n-butylamine, di-n-pentylamine, di-n-hexylamine, di-n-heptylamine, di-n-octylamine, di-n-nonylamine, and di-n-decylamine; trialkylamines such as triethylamine, tri-n-propylamine, tri-n-butylamine, tri-n-pentylamine, tri-n-hexylamine, tri-n-heptylamine, tri-n-octylamine, tri-n-nonylamine, and tri-n-decylamine; aromatic amines such as aniline, N-methylaniline, N,N-dimethylaniline, 2-methylaniline, 3-methylaniline, 4-methylaniline, 4-nitroaniline, diphenylamine, triphenylamine, and 1-naphthylamine; and alkanolamines such as ethanolamine, diethanolamine, and triethanolamine.

Examples of the nitrogen-containing compounds (β) include ethylenediamine, N,N,N',N'-tetramethylethylenediamine, tetramethylenediamine, hexamethylenediamine, N,N,N',N'-tetrakis(2-hydroxyethyl)ethylenediamine, N,N,N',N'-tetrakis(2-hydroxypropyl)ethylenediamine, 4,4'-diaminodiphenylmethane, 4,4'-diamino diphenyl ether, 4,4'-diaminobenzophenone, 4,4'-diaminodiphenylamine, 2,2'-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, and 1,3-bis[1-(4-aminophenyl)-1-methylethyl]benzene.

Examples of the nitrogen-containing compounds (γ) include polyethyleneimine, polyallylamine, and a polymer of N-(2-dimethylaminoethyl)acrylamide.

Examples of the compounds containing an amide group include formamide, N-methylformamide, N,N-dimethylformamide, acetamide, N-methylacetamide, N,N-dimethylacetamide, propionamide, benzamide, pyrrolidone, and N-methylpyrrolidone.

As examples of the urea compound, urea, methylurea, 1,1-dimethylurea, 1,3-dimethylurea, 1,1,3,3-tetramethylurea, 1,3-diphenylurea, and tri-n-butylthiourea can be given.

As examples of the nitrogen-containing heterocyclic compound, imidazoles such as imidazole, benzimidazole, 2-methylimidazole, 4-methylimidazole, 1,2-dimethylimidazole, 2-phenylimidazole, 4-phenylimidazole, 4-methyl-2-phenylimidazole, and 2-phenylbenzimidazole; pyridines such as pyridine, 2-methylpyridine, 4-methylpyridine, 2-ethylpyridine, 4-ethylpyridine, 2-phenylpyridine, 4-phenylpyridine, 2-methyl-4-phenylpyridine, nicotine, nicotinic acid, nicotinamide, quinoline, 8-oxyquinoline, and acridine; pyrazine, pyrazole, pyridazine, quinoxaline, purine, pyrrolidine, piperidine, 1-piperidine ethanol, 2-piperidine ethanol, morpholine, 4-methylmorpholine, piperazine, 1,4-dimethylpiperazine, 1,4-diazabicyclo[2.2.2]octane, and the like can be given.

A compound having an acid-dissociable group can also be used as the nitrogen-containing organic compound.

As examples of the nitrogen-containing organic compound having an acid-dissociable group, N-(t-butoxycarbonyl)piperidine, N-(t-butoxycarbonyl)imidazole, N-(t-butoxycarbonyl)benzimidazole, N-(t-butoxycarbonyl)-2-phenylbenzimidazole, N-(t-butoxycarbonyl)di-n-octylamine, N-(t-butoxycarbonyl)diethanolamine, N-(t-butoxycarbonyl)dicyclohexylamine, and N-(t-butoxycarbonyl)diphenylamine can be given.

Of these nitrogen-containing organic compounds, the nitrogen-containing compounds (α), nitrogen-containing compounds (β), nitrogen-containing heterocyclic compounds, and nitrogen-containing organic compounds having an acid-dissociable group are preferable. The acid diffusion controllers may be used either individually or in combination of two or more.

The amount of the acid diffusion controller to be added is preferably 15 parts by weight or less, more preferably 0.001-10 parts by weight, and particularly preferably 0.005-5 parts by weight for 100 parts by weight of the acid-dissociable group-containing resin (B) or alkali-soluble resin. Incorporating the acid diffusion controller in an amount of 0.001 parts by weight or more prevents deterioration of the pattern shape and size fidelity. Also, incorporating the acid diffusion controller in an amount of 15 parts by weight or less improves the sensitivity as a resist and improves the developability of the exposure area.

A dissolution controller improving the solubility in an alkaline developer by the action of an acid may be added to the positive-tone radiation sensitive resin composition and negative-tone radiation sensitive resin composition of the present invention.

As examples of such a dissolution controller, compounds having an acid functional group such as a phenolic hydroxyl group, carboxyl group, and sulfonic group, compounds in which the hydrogen atom in the acidic functional group is replaced by an acid-dissociable group, and the like can be given.

The dissolution controller may be a low molecular compound or high molecular compound. As the high molecular dissolution controller for the negative-tone radiation sensitive resin composition, the acid-dissociable group containing resin (B) of the positive-tone radiation sensitive resin composition, for example, can be given.

These dissolution controllers may be used either individually or in combination of two or more. The proportion of the dissolution controllers to be added is 50 parts by weight or less, and preferably 20 parts by weight or less for 100 parts by weight of the total resin component in the radiation sensitive resin composition.

A surfactant that improves applicability, developability, striation, and the like may be added to the positive-tone radiation sensitive resin composition and negative-tone radiation sensitive resin composition of the present invention.

As the surfactant, any of anionic surfactants, cationic surfactants, nonionic surfactants, and amphoteric surfactants may be used. Of these, nonionic surfactants are preferable.

As examples of nonionic surfactants, polyoxyethylene higher alkyl ethers, polyoxyethylene higher alkyl phenyl ethers, higher fatty acid diesters of polyethylene glycol, commercially available products such as KP (manufactured by Shin-Etsu Chemical Co., Ltd.), Polyflow (manufactured by Kyoeisha Chemical Co., Ltd.), EFTOP (manufactured by TOHKEM PRODUCTS CORPORATION), MEGAFAC (manufactured by Dainippon Ink and Chemicals, Inc.), Fluorad (manufactured by Sumitomo 3M, Ltd.), Asahi Guard, Surflon (manufactured by Asahi Glass Co., Ltd.), and the like can be given.

These surfactants may be used either individually or in combination of two or more. The proportion of the surfactants to be added is 2 parts by weight or less, and preferably 1.5 parts by weight or less, as an effective component, for 100 parts by weight of the total resin components in the radiation sensitive resin composition.

A sensitizer can be added to the positive-tone radiation sensitive resin composition and negative-tone radiation sensitive resin composition of the present invention. The sensitizer absorbs radiation energy and transmits the energy to the photoacid generator, thereby increasing the amount of an acid to be generated upon exposure and improving the apparent sensitivity of the radiation sensitive resin composition.

As examples of the sensitizer, acetophenones, benzophenones, naphthalenes, biacetyl, eosine, rose bengale, pyrenes, anthracenes, phenothiazines, and the like can be given.

These sensitizers may be used either individually or in combination of two or more. The proportion of the sensitizers to be added is 50 parts by weight or less, and preferably 30 parts by weight or less for 100 parts by weight of the total resin component in the radiation sensitive resin composition.

Other additives may be added to the positive-tone radiation sensitive resin composition and negative-tone radiation sensitive resin composition of the present invention, as required, to the extent that does not impair the effects of the present invention. Examples of such additives include dyes, pigments, adhesion adjuvants, halation inhibitors, preservatives, defoaming agents, and shape improvers. Specific additives include 4-hydroxy-4'-methylchalcone and the like.

Addition of a dye or a pigment visualizes a latent image in the exposed area, thereby decreasing the effects of halation during exposure. Use of an adhesion improver improves adhesion to the substrates.

Preparation of Composition Solution

The positive-tone radiation sensitive resin composition and negative-tone radiation sensitive resin composition of the present invention is usually prepared as a composition solution by dissolving the components in a solvent to obtain a homogeneous solution and, optionally, filtering the solution through a filter with a pore size of about 0.2 μm.

Ethers, esters, ether esters, ketones, ketone esters, amides, amide esters, lactams, and (halogenated) hydrocarbons are given as examples of the solvent which can be used here. Specific examples are ethylene glycol monoalkyl ethers, diethylene glycol dialkyl ethers, propylene glycol monoalkyl ethers, propylene glycol dialkyl ethers, ethylene glycol monoalkyl ether acetates, propylene glycol monoalkyl ether acetates, (non)cyclic ketones, acetates, hydroxy acetates, alkoxy acetates, acetoacetates, propionates, lactates, other substituted propionates, (substituted) butyrates, pyruvates, N,N-dialkyl formamides, N,N-dialkyl acetamides, N-alkylpyrolidones, (halogenated) aliphatic hydrocarbons, and (halogenated) aromatic hydrocarbons.

More specifically, such solvents include ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, propylene glycol monomethyl ether acetate, propylene glycol monoethyl ether acetate, propylene glycol mono-n-propyl ether acetate, methyl ethyl ketone, 2-heptanone, 3-heptanone, 4-heptanone, cyclohexanone, ethyl acetate, n-propyl acetate, n-butyl acetate, isopropenyl acetate, 3-methoxybutyl acetate, 3-methyl-3-methoxybutyl acetate, ethyl hydroxyacetate, ethyl ethoxyacetate, methyl acetoacetate, ethyl acetoacetate, isopropenyl propionate, 3-methyl-3-methoxybutyl propionate, methyl lactate, ethyl lactate, n-propyl lactate, i-propyl lactate, methyl 3-methoxy propionate, ethyl 3-methoxypropionate, methyl 3-ethoxypropionate, ethyl 3-ethoxypropionate, 3-methyl-3-methoxybutyl butyrate, methyl 2-hydroxy-3-methylbutyrate, ethyl 2-hydroxy-2-methyl propionate, N,N-dimethyl formamide, N,N-dimethyl acetamide, N-methyl pyrolidone, toluene, and xylene.

Of these solvents, propylene glycol monoalkyl ether acetates, 2-heptanone, lactates, 2-hydroxypropionates, 3-alkoxypropionates, and the like are desirable to ensure excellent uniformity of the film surface during application.

These solvents may be used either individually or in combination of two or more.

One or more solvents with a high boiling point may optionally be added to the solvent. Examples of such solvents with a high boiling point include benzyl ethyl ether, di-n-hexyl ether, diethylene glycol monomethyl ether, diethylene glycol monoethyl ether, acetonylacetone, isophorone, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, propylene carbonate, and ethylene glycol monophenyl ether acetate.

These other solvents may be used either individually or in combination of two or more.

The proportion of the other solvents to be added is 50 wt % or less, and preferably 30 wt % or less of the total amount of solvents used.

The solvents are used in a total amount to make the total solid content of the solution composition usually 5-50 wt %, preferably 10-50 wt %, more preferably 10-40 wt %, and particular preferably 10-30 wt %. An optimal solid content is 10-25 wt %. The total solid content in the above range is desirable to ensure excellent uniformity of the film surface during application.

Formation of Resist Pattern

A resist pattern is formed from the positive-tone radiation sensitive resin composition and negative-tone radiation sensitive resin composition of the present invention by applying the composition solution thus prepared to, for example, substrates such as a silicon wafer or a wafer coated with aluminum using an appropriate application method such as rotational coating, cast coating, and roll coating to form a resist film. Then, after optional heat treatment (hereinafter referred to as "PB"), the resist film is exposed to radiation through a mask with a prescribed pattern.

As radiation that can be used here, deep ultraviolet rays such as a bright line spectrum of a mercury lamp (wavelength: 254 nm), KrF excimer laser (wavelength: 248 nm), ArF excimer laser (wavelength: 193 nm), $F_2$ excimer laser (wavelength: 157 nm), and EUV (wavelength: 13 nm); X-rays such as synchrotron radiation, charged particle rays such as electron beams, and the like can be used according to the types of photoacid generators. Deep ultraviolet rays and charged particle rays are preferable, with KrF excimer laser (wavelength: 248 nm), ArF excimer laser (wavelength: 193 nm), $F_2$ excimer laser (wavelength: 157 nm), and electrom beams being particularly preferable.

The exposure conditions such as the dose of radiation are appropriately determined according to the composition of the positive-tone radiation sensitive resin composition and negative-tone radiation sensitive resin composition, types of additives, and the like.

When forming a resist pattern, post exposure bake (hereinafter called "PEB") which is a heat treatment after exposure is preferable to increase apparent sensitivity of the resist.

PEB is performed at a temperature of 30-200° C., and preferably 50-150° C., although the temperature varies depending on the composition of the radiation sensitive resin composition, types of additives, and the like.

The resist film after exposure is developed in an alkaline developer to form a predetermined positive-tone and negative-tone resist pattern.

As the alkaline developer, an alkaline aqueous solution in which one or more alkaline compounds such as an alkaline metal hydroxide, aqueous ammonia, alkylamines, alkanolamines, heterocyclic amines, tetraalkylammonium hydroxides, choline, 1,8-diazabicyclo[5.4.0]-7-undecene, and 1,5-diazabicyclo[4.3.0]-5-nonene are dissolved is used. An aqueous solution of tetraalkylammonium hydroxide is a particularly preferable alkaline developer.

The concentration of the alkaline aqueous solution is preferably 10 wt % or less, more preferably 1-10 wt %, and particularly preferably 2-5 wt %. The concentration of the alkaline aqueous solution less than 10 wt % prevents dissolution of an unexposed area in the developer.

The addition of an appropriate amount of a surfactant to the alkaline aqueous solution is desirable to increase wettability of the resist film to the developer.

After development using the alkaline aqueous solution developer, the resist film is generally washed with water and dried.

BEST MODE FOR CARRYING OUT THE INVENTION

Figure 1:
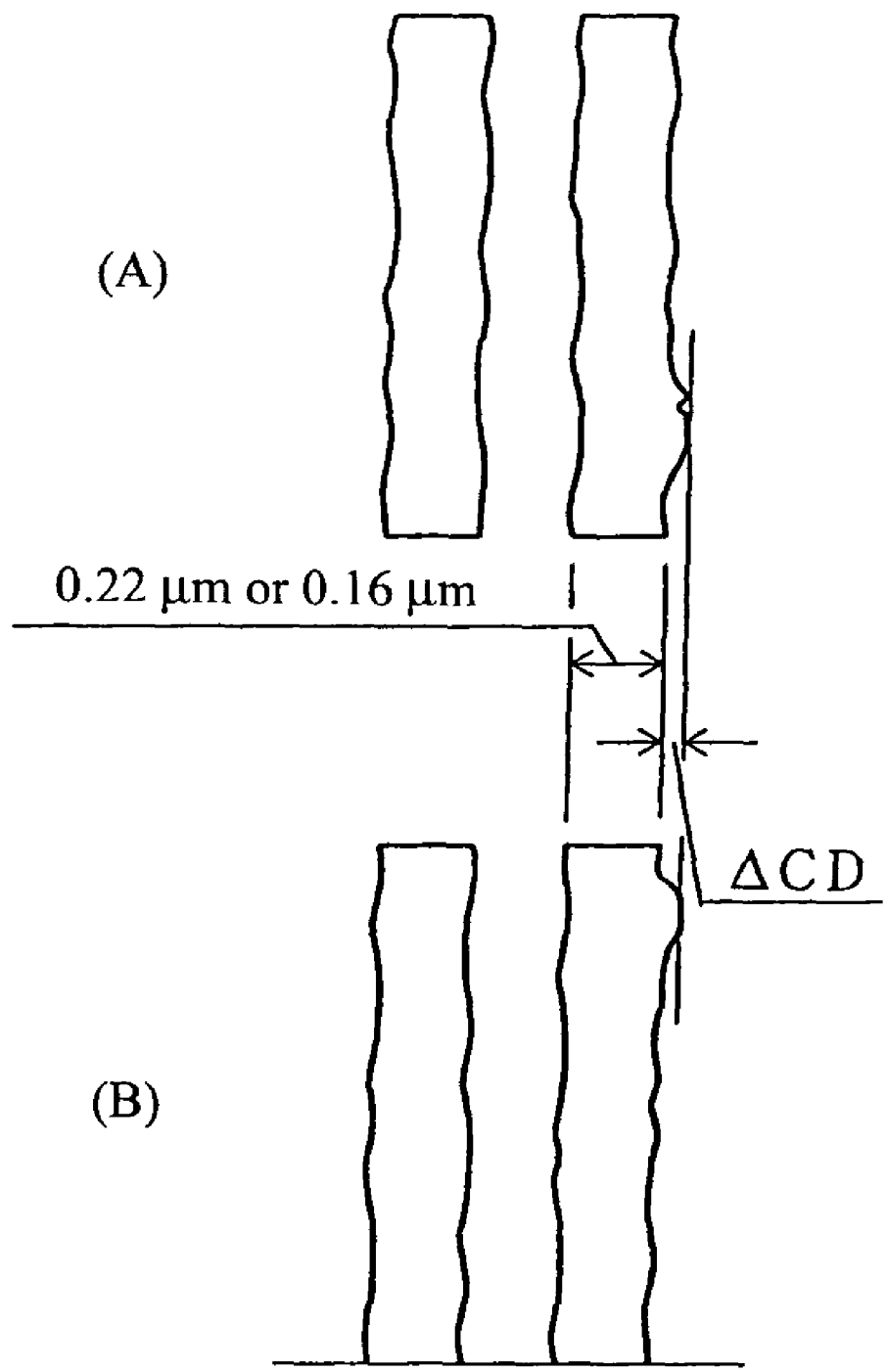
FIG. 1 shows an evaluation standard for nano edge roughness.

The present invention will be described in more detail by way of examples. However, these examples should not be construed as limiting the present invention.

In the examples, part(s) and % refer to part(s) by weight and wt % unless otherwise indicated.

The following acid generators (A-1)-(A-4) were subjected to mass spectrometry under the following conditions.
Apparatus: JMS-AX 505 W type mass spectrometer manufactured by the JEOL Ltd.
Emitter current: 5 mA (gas: Xe)
Acceleration voltage: 3.0 kV
10 N MULTI: 1.3
Ionization method: Fast atom bombardment (FAB) method
Detected ion: cation (+)
Measured mass range: 20-1,500 m/z
Scanning: 30 sec
Resolving power: 1,500
Matrix: 3-Nitrobenzyl alcohol The acid generators (A-1) to (A-4) were subjected to $^1$H-NMR analysis using JNM-EX270 manufactured by JEOL Ltd. and CDCl$_3$ as a measuring solvent.
Synthesis of Acid Generator (I)

Synthesis Example 1

After charging 69.6 g of sodium dithionite and 50.4 g of sodium hydrogencarbonate to a 2l three-mouthed flask fully substituted with nitrogen, 600 ml of dimethylsulfoxide and 47.8 g of 1-bromo 1,1-difluoro-2-(bicyclo[2.2.1]heptan-2-yl) ethane were added one after the other at room temperature and the mixture was stirred at 80° C. in a nitrogen atmosphere for five hours. Next, after distilling the reaction solution under reduced pressure to extract the dimethylsulfoxide, 300 g of ion-exchanged water, 350 mg of sodium tungstate dihydrate, and 5.0 g of disodium hydrogenphosphate were added, and while maintaining the pH of the reaction solution, 5.6 ml of a 30% hydrogen peroxide solution was carefully added dropwise at room temperature. The mixture was stirred at 60° C. for one hour. The obtained mixture was distilled under vacuum to remove the water, the resulting residue was extracted with methanol twice, and the methanol was removed by vacuum distillation to obtain 27.3 g of sodium 1,1-difluoro-2-(bicyclo[2.2.1]heptan-2-yl)ethane sulfonate (hereinafter referred to as "compound (a)").

A solution of 7.0 g of triphenylsulfonium bromide dissolved in 75 ml of ion-exchanged water was charged to a 200 ml eggplant flask, 5.0 g of the compound (a) and 75 ml of methylene chloride were added to the solution at room temperature, and the mixture was stirred at the same temperature for one hour. The organic layer was separated, washed with ion-exchanged water five times, and distilled under vacuum to obtain 8.35 g of triphenylsulfonium 1,1-difluoro-2-(bicyclo[2.2.1]heptan-2-yl)ethane sulfonate as a white solid.

This compound is indicated as "acid generator (A-1)".

Results of mass spectrometry of the acid generator (A-1) show that the anion moiety was m/z=239 (M$^+$).

The following are the results of $^1$H-NMR analysis (chemical shift Δ(ppm)) of the acid generator (A-1).
7.80-7.65 (15H)
2.45-2.06 (4H)
1.94-1.77 (1H)
1.58-0.74 (8H)

Synthesis Example 2

After charging 4 g of 1-n-butoxynaphthalene and 10.6 g of a phosphorous pentaoxide-methansulfonate mixture to a 300 ml eggplant flask and stirring the mixture for 15 minutes at room temperature, 2.4 g of tetramethylenesulfoxide was added dropwise at 0° C. and the mixture was stirred for 20 minutes. After gradually increasing the temperature to room temperature and stirring for a further one hour, the reaction solution was once again cooled to 0° C. After the addition of 100 ml of distilled water, the mixture was adjusted to pH 7.0 using 25% ammonia water and stirred for one hour at room temperature. Next, the reaction solution was washed with ether, 5.0 g of compound (a) and 100 ml of methylene chloride were added at room temperature. The mixture was stirred at the same temperature for one hour. The organic layer was separated, washed with ion-exchanged water five times, and concentrated under vacuum. The concentrate was reprecipitated with methylene chloride/n-hexane to obtain 8.25 g of 1-(4-n-butoxynaphthalen-1-yl)tetrahydrothiophenium 1,1-difluoro-2-(bicyclo[2.2.1]heptan-2-yl)ethanesulfonate.

This compound is indicated as "acid generator (A-2)".

Results of mass spectrometry of the acid generator (A-2) show that the anion moiety was m/z=239 (M$^+$).

The following are the results of $^1$H-NMR analysis (chemical shift Δ(ppm)) of the acid generator (A-2).
8.39 (1H)
8.28 (1H)
7.99 (1H)
7.75 (1H)
7.63 (1H)
7.05 (1H)
4.35 (2H)
4.22 (2H)
3.71 (2H)
2.62 (4H)
2.07-2.47 (4H)
1.77-1.98 (4H)
0.74-1.66 (12H)

Synthesis Example 3

A solution of 6.45 g of diphenyliodonium chloride dissolved in 100 ml of ion-exchanged water was charged to a 300 ml eggplant flask, 5.0 g of the compound (a) and 100 ml of methylene chloride was added to the solution at room temperature, and the mixture was stirred at the same temperature for one hour. The organic layer was separated, washed with ion-exchanged water five times, and concentrated under vacuum to obtain 8.1 g of diphenyliodonium 1,1-difluoro-2-(bicyclo[2.2.1]heptan-2-yl)ethane sulfonate as a white solid.

This compound is indicated as "acid generator (A-3)".

Results of mass spectrometry of the acid generator (A-3) show that the anion moiety is m/z=239 ($M^+$).

The following are the results of $^1$H-NMR analysis (chemical shift Δ(ppm)) of the acid generator (A-3).

8.03 (4H)
7.56 (2H)
7.41 (4H)
2.15-1.72 (5H)
1.49-0.61 (8H)

Synthesis Example 4

After charging 69.6 g of sodium dithionite and 50.4 g of sodium hydrogencarbonate to a 2 l three-necked flask fully substituted with nitrogen, 600 ml of dimethylsulfoxide and 47.8 g of 1-bromo-1,1-difluoro-2-(bicyclo[2.2.1]heptan-2-yl)ethane were added one after the other at room temperature and the mixture was stirred at 80° C. in nitrogen atmosphere for five hours. The reaction solution was concentrated under vacuum to remove the dimethylsulfoxide, 300 g of ion-exchanged water was added to the residue, the water layer was extracted four times with ethyl acetate, and the organic layer was washed three times with saturated brine. The ethyl acetate was removed by concentration under vacuum to obtain 31.3 g of sodium 1,1-difluoro-2-(bicyclo[2.2.1]heptan-2-yl)ethane sulfinate (hereinafter referred to as "compound (b)").

A solution of 30 g of the compound (b) dissolved in 100 ml of ion-exchanged water was charged to a 300 ml eggplant flask and cooled to 5° C., followed by bubbling with chlorine gas for 15 or more minutes at the same temperature. The water layer was removed by decantation, the oily substance remaining on the bottom of the flask was extracted with methylene chloride, and the organic layer was washed twice with a saturated sodium hydrogencarbonate aqueous solution and dried over anhydrous magnesium sulfate. The methylene chloride was removed by concentration under vacuum to obtain 24.5 g of 1,1-difluoro-2-(bicyclo[2.2.1]heptan-2-yl)ethane sulfonylchloride (hereinafter referred to as "compound (c)").

A 500 ml eggplant flask was charged with 24.0 g of the compound (c), 180 g of acetone, and 17.0 g of N-hydroxybicyclo[2.2.1]hept-5-ene-2,3-dicarboxyimide in sequence and cooled to 5° C. While maintaining the mixture at 5° C., a solution of 10 g of triethylamine dissolved in 20 g of acetone was added dropwise, and the solution was stirred for five hours at the same temperature. The reaction solution was added dropwise to a large amount of water, the resulting precipitate was recrystallized with acetone/water two times, and the resulting crystals were dissolved in methylene chloride. The organic layer was sequentially washed with a 5% oxalic acid aqueous solution and ion-exchanged water and concentrated under vacuum to remove the methylene chloride to obtain 16.8 g of N-{1,1-difluoro-2-(bicyclo[2.2.1]heptan-2-yl)ethansulfonyloxy}bicyclo[2.2.1]hept-5-ene-2,3-dicarboxyimide.

This compound is indicated as "acid generator (A-4)".

The results of mass spectrometry of the acid generator (A-4) was m/z=402 ($M^++1$).

The following are the results of $^1$H-NMR analysis (chemical shift Δ(ppm)) of the acid generator (A-4).

6.19 (2H)
3.49 (2H)
3.35 (2H)
2.67-2.08 (5H)
1.82-0.76 (10H)

<Synthesis of Acid-Dissociable Group-Containing Resin (B)>

Synthesis Example 5

101 g of 4-acetoxystyrene, 5 g of styrene, 42 g of 4-t-butoxystyrene, 6 g of azobisisobutylonitrile (AIBN), and 1 g of t-dodecylmercaptan were dissolved in 160 g of propylene glycol monomethyl ether. The mixture was polymerized for 16 hours at 70° C. in a nitrogen atmosphere. After polymerization for 16 hours, the reaction solution was added dropwise to a large quantity of n-hexane to coagulate and purify the resulting resin.

After the addition of 150 g of propylene glycol monomethyl ether to the resin, 300 g of methanol, 80 g of triethylamine, and 15 g of water were added. The mixture was hydrolyzed for 8 hours while refluxing at the boiling point. After the reaction, the solvent and triethylamine were evaporated under reduced pressure. The resulting resin was dissolved in acetone and added dropwise to a large quantity of water to coagulate the resin. The resulting white powder was filtered and dried overnight at 50° C. under reduced pressure.

The resin was found to have Mw and Mw/Mn of 16,000 and 1.7 respectively. The result of $^{13}$C-NMR analysis confirmed that the resin was a copolymer of 4-hydroxystyrene, styrene, and 4-t-butoxystyrene at a copolymerization molar ratio of 72:5:23.

This resin is referred to as a "resin (B-1)".

Mw and Mn of the resin (B-1) and the following resins (B-2)-(B-11) were measured by gel permeation chromatography (GPC) using GPC columns (manufactured by Tosoh Corp., G2000H$_{XL}$×2, G3000H$_{XL}$×1, G4000H$_{XL}$×1) under the following conditions. Flow rate: 1.0 ml/minute, eluate: tetrahydrofuran, column temperature: 40° C., standard reference material: monodispersed polystyrene

Synthesis Example 6

100 g of 4-acetoxystyrene, 25 g of t-butyl acrylate, 18 g of styrene, 6 g of AIBN, and 1 g of t-dodecylmercaptan were dissolved in 230 g of propylene glycol monomethyl ether. The mixture was polymerized for 16 hours at 70° C. in a nitrogen atmosphere. After polymerization, the reaction solution was added dropwise to a large quantity of n-hexane to coagulate and purify the resulting resin.

After the addition of 150 g of propylene glycol monomethyl ether to the resin, 300 g of methanol, 80 g of triethylamine, and 15 g of water were added. The mixture was hydrolyzed for 8 hours while refluxing at the boiling point. After the reaction, the solvent and triethylamine were evaporated under reduced pressure. The resulting resin was dissolved in acetone and added dropwise to a large quantity of water to coagulate the resin. The resulting white powder was filtered and dried overnight at 50° C. under reduced pressure.

The resin was found to have Mw and Mw/Mn of 11,500 and 1.6 respectively. The result of $^{13}$C-NMR analysis confirmed that the resin was a copolymer of 4-hydroxystyrene, t-butyl acrylate, and styrene at a copolymerization molar ratio of 61:19:20.

This resin is referred to as a "resin (B-2)".

Synthesis Example 7

176 g of 4-t-butoxystyrene was anionically polymerized at −78° C. in 500 ml of tetrahydrofuran using n-butyllithium as a catalyst. After polymerization, the resulting resin solution was coagulated in methanol to obtain 150 g of white poly(4-t-butoxystyrene).

150 g of poly(4-t-butoxystyrene) was dissolved in 600 g of dioxane. After the addition of diluted hydrochloric acid, the mixture was hydrolyzed at 70° C. for 2 hours. The reaction solution was added dropwise into a large quantity of methanol to coagulate the resin. A step of dissolving the coagulated resin in acetone and adding dropwise to a large quantity of water to coagulate the resin was repeated. The resulting white powder was filtered and dried overnight at 50° C. under reduced pressure.

The Mw and Mw/Mn of this resin were 10,400 and 1.10, respectively. $^{13}$C-NMR analysis confirmed that the resin is a copolymer of 4-t-butoxystyrene and 4-hydroxystyrene at a copolymerization molar ratio of these monomers of 68:32, in which only part of t-butyl group in the poly(4-t-butoxystyrene) had a hydrolyzed structure.

This resin is referred to as a "resin (B-3)".

Synthesis Example 8

25 g of a copolymer of 4-hydroxystyrene and 4-t-butoxystyrene (copolymerization molar ratio: 90:10) was dissolved in 100 g of n-butyl acetate. Nitrogen gas was bubbled through the solution for 30 minutes. After the addition of 3.3 g of ethyl vinyl ether and 1 g of pyridinium p-toluenesulfonate as a catalyst, the mixture was reacted at room temperature for 12 hours. The reaction solution was dropped into a 1% ammonium aqueous solution to coagulate the resin. The resin was filtered and dried overnight at 50° C. under reduced pressure.

Mw and Mw/Mn of this resin were respectively 13,000 and 1.01. As a result of $^{13}$C-NMR analysis, the resin was found to have a structure in which 23 mol % of hydrogen atoms of the phenolic hydroxyl group in poly(4-hydroxystyrene) was replaced by ethoxyethyl groups, and 10 mol % by t-butyl groups.

This resin is referred to as a "resin (B-4)".

Synthesis Example 9

A monomer solution was prepared by dissolving 53.69 g of 5-oxo-4-oxatricyclo[4.2.1.0$^{3,7}$]nonan-2-yl methacrylate and 46.31 g of 2-methyladamantan-2-yl methacrylate in 200 g of 2-butanone, and further adding 4.04 g of dimethylazobisisobutyrate.

A 1,000 ml three-necked flask containing 100 g of 2-butanone was purged with nitrogen for 30 minutes. Then, while the contents were heated to 80° C. with stirring, the above monomer solution was added dropwise over four hours using a dropping funnel. Polymerization was initiated at the start of dropping and continued for six hours. After the polymerization, the polymer solution was cooled with water to 30° C. or lower and poured into 2,000 g of methanol. White precipitate produced was collected by filtration. The resulting white powder was washed twice with 400 g of methanol in the form of a slurry, filtered, and dried under reduced pressure for 17 hours at 50° C. to obtain a white resin powder.

The resin was found to have Mw and Mw/Mn of 9,700 and 2.14, respectively. The result of $^{13}$C-NMR analysis confirmed that the resin was a copolymer of 5-oxo-4-oxatricyclo[4.2.1.0$^{3,7}$]nonan-2-yl methacrylate and 2-methyladamantan-2-yl methacrylate at a copolymerization molar ratio of 59.6:40.4.

This resin is referred to as a "resin (B-5)".

Synthesis Example 10

A monomer solution was prepared by dissolving 40.90 g of 2-methyladamantan-2-yl methacrylate, 15.47 g of 3-hydroxyadamantan-1-yl methacrylate, and 43.64 g of 5-oxo-4-oxatricyclo[4.2.1.0$^{3,7}$]nonan-2-yl methacrylate in 200 g of 2-butanone, and further adding 4.02 g of dimethylazobisbutyrate.

A 1,000 ml three-necked flask containing 100 g of 2-butanone was purged with nitrogen for 30 minutes. Then, while the contents were heated to 80° C. with stirring, the above monomer solution was added dropwise over four hours using a dropping funnel. Polymerization was initiated at the start of dropping and continued for six hours. After the polymerization, the polymer solution was cooled with water to 30° C. or lower and poured into 2,000 g of methanol. White precipitate produced was collected by filtration. The resulting white powder was washed twice with 400 g of methanol in the form of a slurry, filtered, and dried under reduced pressure for 17 hours at 50° C. to obtain a white resin powder.

The resin was found to have Mw and Mw/Mn of 9,200 and 2.00 respectively. The result of $^{13}$C-NMR analysis confirmed that the resin was a copolymer of 2-methyladamantan-2-yl methacrylate, 3-hydroxyadamantan-1-yl methacrylate, and 5-oxo-4-oxatricyclo[4.2.1.0$^{3,7}$]nonan-2-yl methacrylate at a copolymerization molar ratio of 36.2:15.2:48.6.

This resin is referred to as a "resin (B-6)".

Synthesis Example 11

A monomer solution was prepared by dissolving 43.66 g of 1-(adamantan-1-yl)-1-methylethyl methacrylate, 14.74 g of 3-hydroxyadamantan-1-yl methacrylate, and 43.66 g of 5-oxo-4-oxatricyclo[4.2.1.0$^{3,7}$]nonan-2-yl methacrylate in 200 g of 2-butanone, and further adding 3.83 g of dimethylazobisbutyrate.

A 1,000 ml three-necked flask containing 100 g of 2-butanone was purged with nitrogen for 30 minutes. Then, while the contents were heated to 80° C. with stirring, the above monomer solution was added dropwise over four hours using a dropping funnel. Polymerization was initiated at the start of dropping and continued for six hours. After the polymerization, the polymer solution was cooled with water to 30° C. or lower and poured into 2,000 g of methanol. White precipitate produced was collected by filtration. The resulting white powder was washed twice with 400 g of methanol in the form of a slurry, filtered, and dried under reduced pressure for 17 hours at 50° C. to obtain a white resin powder.

The resin was found to have Mw and Mw/Mn of 9,600 and 1.96, respectively. The result of $^{13}$C-NMR analysis confirmed that the resin was a copolymer of 1-(adamantan-1-yl)-1-methylethyl methacrylate, 3-hydroxyadamantan-1-yl methacrylate, and 5-oxo-4-oxatricyclo[4.2.1.0$^{3,7}$]nonan-2-yl methacrylate at a copolymerization molar ratio of 35.6:15.1:49.3.

This resin is referred to as a "resin (B-7)".

Synthesis Example 12

A monomer solution was prepared by dissolving 16.13 g of 2-ethyladamantan-2-yl methacrylate, 40.58 g of 2-methyladamantan-2-yl methacrylate, and 3.29 g of 5-oxo-4-oxatricyclo[4.2.1.0$^{3,7}$]nonan-2-yl methacrylate in 200 g of 2-butanone, and further adding 3.99 g of dimethylazobisisobutyrate.

A 1,000 ml three-necked flask containing 100 g of 2-butanone was purged with nitrogen for 30 minutes. Then, while the contents were heated to 80° C. with stirring, the above monomer solution was added dropwise over four hours using a dropping funnel. Polymerization was initiated at the start of dropping and continued for six hours. After the polymerization, the polymer solution was cooled with water to 30° C. or lower and poured into 2,000 g of methanol. White precipitate produced was collected by filtration. The resulting white powder was washed twice with 400 g of methanol in the form of a slurry, filtered, and dried under reduced pressure for 17 hours at 50° C. to obtain a white resin powder.

The resin was found to have Mw and Mw/Mn of 8,900 and 2.00, respectively. The result of $^{13}$C-NMR analysis confirmed that the resin was a copolymer of 2-ethyladamantan-2-yl methacrylate, 2-methyladamantan-2-yl methacrylate, and 5-oxo-4-oxatricyclo[4.2.1.0$^{3,7}$]nonan-2-yl methacrylate at a copolymerization molar ratio of 13.7:38.2:48.1.

This resin is referred to as a "resin (B-8)".

Synthesis Example 13

A monomer solution was prepared by dissolving 42.44 g of 5-oxo-4-oxatricyclo[4.2.1.0$^{3,7}$]nonan-2-yl acrylate, 15.10 g of 3-hydroxyadamantan-1-yl acrylate, and 42.46 g of 2-ethyladamantan-2-yl acrylate in 200 g of 2-butanone, and further adding 4.17 g of dimethylazobisbutyrate. A 1,000 ml three-necked flask containing 100 g of 2-butanone was purged with nitrogen for 30 minutes. Then, while the contents were heated to 80° C. with stirring, the above monomer solution was added dropwise over four hours using a dropping funnel. Polymerization was initiated at the start of dropping and continued for six hours. After the polymerization, the polymer solution was cooled with water to 30° C. or lower and poured into 2,000 g of methanol. White precipitate produced was collected by filtration. The resulting white powder was washed twice with 400 g of methanol in the form of a slurry, filtered, and dried under reduced pressure for 17 hours at 50° C. to obtain a white resin powder.

The resin was found to have Mw and Mw/Mn of 10,200 and 1.75, respectively. The result of $^{13}$C-NMR analysis confirmed that the resin was a copolymer of 5-oxo-4-oxatricyclo [4.2.1.0$^{3,7}$]nonan-2-yl acrylate, 3-hydroxyadamantan-1-yl acrylate, and 2-ethyladamantan-2-yl acrylate at a copolymerization molar ratio of 49.2:15.3:35.5.

This resin is referred to as a "resin (B-9)".

Synthesis Example 14

A monomer solution was prepared by dissolving 55.00 g of 5-oxo-4-oxatricyclo[4.2.1.0$^{3,7}$]nonan-2-yl methacrylate, 11.70 g of 3-hydroxyadamantan-1-yl methacrylate, and 33.31 g of 1-ethylcyclopentyl acrylate in 200 g of 2-butanone, and further adding 4.56 g of dimethylazobisbutyrate.

A 1,000 ml three-necked flask containing 100 g of 2-butanone was purged with nitrogen for 30 minutes. Then, while the contents were heated to 80° C. with stirring, the above monomer solution was added dropwise over four hours using a dropping funnel. Polymerization was initiated at the start of dropping and continued for six hours. After the polymerization, the polymer solution was cooled with water to 30° C. or lower and poured into 2,000 g of methanol. White precipitate produced was collected by filtration. The resulting white powder was washed twice with 400 g of methanol in the form of a slurry, filtered, and dried under reduced pressure for 17 hours at 50° C. to obtain a white resin powder.

The resin was found to have Mw and Mw/Mn of 8,500 and 1.75, respectively. The result of $^{13}$C-NMR analysis confirmed that the resin was a copolymer of 5-oxo-4-oxatricyclo [4.2.1.0$^{3,7}$]nonan-2-yl methacrylate, 3-hydroxyadamantan-1-yl methacrylate, and 1-ethylcyclopentyl acrylate at a copolymerization molar ratio of 53.7:11.1:35.2.

This resin is referred to as a "resin (B-10)".

Synthesis Example 15

A three-necked flask was charged with 1.52 g of the silane compound of the following formula (27), 1.57 g of the silane compound of the following formula (28), 1.91 g of methyltriethoxysilane, 15 g of 4-methyl-2-pentanone, and 1.31 g of a 1.75 wt % aqueous solution of oxalic acid. The mixture was reacted for 6 hours at 80° C. while stirring, followed by cooling with ice to terminate the reaction. The reaction mixture was poured into a separating funnel to remove the water layer. The organic layer was washed with ion-exchanged water until the reaction solution became neutral. The solvent was evaporated under reduced pressure to obtain a resin.

The resin was found to have a Mw of 2,500 and to comprise the structural unit of the above formula (20-2) and the structural unit of the above formula (22-1) at a molar ratio of 54.7:45.3.

This resin is referred to as a "resin (B-11)".

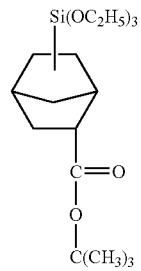

(27)

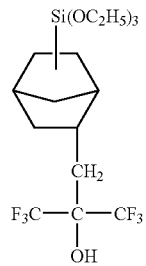

(28)

Evaluation of the resists was carried out as follows.

Sensitivity:

Sensitivity was evaluated based on an optimum exposure dose which is a dose capable of forming a 1:1 line and space pattern (1L1S) with a line width of 0.22 μm when a resist coating formed on a silicon wafer is exposed to light other than ArF excimer laser and a line width of 0.16 μm when exposed to ArF excimer laser, immediately followed by PEB, development in alkali, washing with water, and drying.

Resolution:

The minimum line and space (1L1S) dimension resolved by an optimum dose of irradiation was taken as the resolution.

Mask Pattern Dependability:

When forming a 1L10S pattern with a design width of 0.22 μm (0.22 μm line/2.2 μm space) by exposure to an optimal dose of light other than ArF excimer laser, and when forming a 1L10S pattern with a design width of 0.16 μm (0.16 μm line/1.6 μm space) by exposure to an optimal dose of ArF excimer laser, a resulting line pattern with a line width greater than 70% of the design width (0.22 μm) was judged as "good" and a line width of 70% or less of the design width was judged as "bad".

Mask Pattern Faithfulness:

When forming a 1L5S pattern with a design width of 0.22 μm (0.22 μm line/1.1 μm space) using an optimal dose of light other than ArF excimer laser, and when forming a 1L5S pattern with a design width of 0.16 μm (0.16 μm line/0.80 μm space) using an optimal dose of ArF excimer laser, the difference of the line width of the resulting line pattern and the design width (absolute value) was regarded as the mask pattern faithfulness.

Nano-Edge Roughness

A 1L1S line pattern with a designed line width of 0.22 μm, when using light other than ArF excimer laser, was observed by a scanning electron microscope to measure a dimension ΔCD (absolute value), which is a maximum projection from the designed line width of 0.22 μm in the irregularity produced along the side of the line pattern, as shown in FIG. 1 (wherein the roughness is magnified). A ΔCD less than 0.044 μm was judged as "good" and a ΔCD of or 0.044 μm or more was judged as "bad".

A 1L1S line pattern with a designed line width of 0.16 μm, when using ArF excimer laser, was observed by a scanning electron microscope to measure a dimension ΔCD (absolute value), which is a maximum projection from the designed line width of 0.16 μm in the irregularity produced along the side of the line pattern, as shown in FIG. 1. A ΔCD less than 0.032 μm was judged as "good" and a ΔCD of or 0.032 μm or more was judged as "bad".

Examples 1-20 and Comparative Examples 1-5

Components shown in Tables 1 and 2 were mixed to prepare homogeneous solutions. The solutions were filtered through a membrane filter with a pore diameter of 0.2 μm to obtain composition solutions. The solution compositions were spin-coated on a silicon wafer. PB was then performed under the conditions shown in Table 3 to form resist coatings with a thickness indicated in Table 3.

The resist coatings were exposed using a Stepper NSR2205 EX12B (numerical aperture: 0.55, manufactured by Nikon Corp.) as the KrF excimer laser (indicated by "KrF" in Table 2); ArF excimer laser photolithography machine (numerical aperture: 0.55, manufactured by Nikon Corp.) as the ArF excimer laser (indicated by "ArF" in Table 2); F$_2$ excimer laser photolithography machine XLS (numerical aperture: 0.60, manufactured by Ultratech) as the F$_2$ excimer laser; Electron Beam Direct Writing System HL700 (acceleration voltage: modified from 30 KeV to 50 KeV, manufactured by Hitachi, Ltd.) as the electron beam, and PEB was performed under the conditions shown in Table 3. The resist patterns were obtained by developing the resist at 23° C. for 1 minute by a paddle method using a 2.38% tetramethylammonium hydroxide aqueous solution, followed by washing with purified water and drying. The results of the evaluation of each resist are shown in Table 4.

Examples 21-26 and Comparative Examples 6-8

Components shown in Table 5 were mixed to prepare homogeneous solutions. The solutions were filtered through a membrane filter with a pore diameter of 0.2 μm to obtain solution compositions. The solution compositions were spin-coated on a silicon wafer. PB was then performed under the conditions shown in Table 6 to form resist coatings with a thickness indicated in Table 6.

The resist coatings were exposed using a Stepper NSR2205 EX12B (numerical aperture: 0.55, manufactured by Nikon Corp.) as the KrF excimer laser (indicated by "KrF" in Table 6) and an ArF excimer laser photolithography machine (numerical aperture: 0.55, manufactured by Nikon Corp.) as the ArF excimer laser (indicated by "ArF" in Table 6) and PEB was performed under the conditions shown in Table 6. The resist patterns were obtained by developing the resist at 23° C. for 1 minute by a paddle method using a 2.38% tetramethylammonium hydroxide aqueous solution, followed by washing with purified water and drying. The results of the evaluation of each resist are shown in Table 7.

Components other than the acid generators (A-1)-(A-4) and the resins (B-1)-(B-11) shown in Tables 1, 2, and 5 are as follows.

Other Acid Generators
    a-1: N-(trifluoromethylsulfonyloxy)bicyclo[2.2.1]hept-5-ene-2,3-dicarboxyimide
    a-2: triphenylsulfonium nonafluoro-n-butanesulfonate
    a-3: triphenylsulfonium perfluoro-n-octanesulfonate
    a-4: 1-(4-n-butoxynaphthalen-1-yl)tetrahydrothiophenium nonafluoro-n-butanesulfonate
    a-5: 1-(4-n-butoxynaphthalen-1-yl)tetrahydrothiophenium perfluoro-n-octanesulfonate
    a-6: bis(cyclohexylsulfonyl)diazomethane Alkali-Soluble Resin
    C-1: 4-Hydroxystyrene/styrene copolymer (copolymerization ratio: 78:22, Mw=3,100, Mw/Mn=1.13)

Crosslinking Agent
    D-1: N,N,N,N-tetra(methoxymethyl)glycoluril

Acid Diffusion Controller
    E-2: triethanolamine
    E-3: 2-phenylbenzimidazole
    E-4: 1,2-dimethylimidazole
    E-5: N-t-butoxycarbonyl 2-phenylbenzimidazole Other Additives
    F-1: t-butoxycarbonylmethyl deoxycholate Solvent
    S-1: ethyl lactate
    S-2: ethyl 3-ethoxypropionate
    S-3: propylene glycol monomethyl ether acetate
    S-4: 2-heptanone
    S-5: cyclohexanone
    S-6: γ-butyrolacton

TABLE 1

|  | Acid generator | Resin | Acid diffusion controller | Crosslinking agent | Other additives | Solvent |
|---|---|---|---|---|---|---|
| Example 1 | A-1 (3) | B-1 (100) | E-2 (0.1) | — | — | S-1 (800) |
| Example 2 | A-2 (3) | B-1 (100) | E-3 (0.1) | — | — | S-1 (800) |

TABLE 1-continued

| | Acid generator | Resin | Acid diffusion controller | Crosslinking agent | Other additives | Solvent |
|---|---|---|---|---|---|---|
| Example 3 | A-3 (3) | B-1 (100) | E-3 (0.2) | — | — | S-1 (800) |
| Example 4 | A-4 (3) | B-1 (100) | E-5 (0.2) | — | — | S-1 (400) S-3 (400) |
| Example 5 | A-3 (1) a-1 (6) | B-1 (100) | E-5 (0.2) | — | — | S-1 (400) S-3 (400) |
| Example 6 | A-3 (2) | B-2 (100) | E-2 (0.1) | — | — | S-1 (400) S-2 (400) |
| Example 7 | A-3 (2) | B-3 (100) | E-3 (0.1) | — | — | S-1 (400) S-3 (400) |
| Example 8 | A-1 (2) | B-4 (100) | E-1 (0.1) | — | — | S-1 (400) S-3 (400) |
| Example 9 | A-1 (2) | B-5 (100) | E-2 (0.1) | — | — | S-3 (700) S-6 (50) |
| Example 10 | A-2 (5) | B-5 (92) | E-3 (0.15) | — | F-1 (8) | S-3 (700) S-6 (50) |
| Example 11 | A-1 (2) a-4 (3) | B-5 (100) | E-3 (0.2) | — | — | S-3 (700) S-6 (50) |
| Example 12 | A-2 (3) a-2 (1) | B-5 (100) | E-2 (0.15) | — | — | S-3 (700) S-6 (50) |
| Example 13 | A-1 (1) A-2 (4) | B-6 (100) | E-3 (0.1) | — | — | S-1 (250) S-3 (550) |
| Example 14 | A-1 (2.5) | B-7 (100) | E-2 (0.1) | — | — | S-4 (500) S-5 (100) |
| Example 15 | A-2 (5.5) | B-8 (100) | E-5 (0.1) | — | — | S-4 (500) S-5 (100) |

(values in parenthesis are parts by weight)

TABLE 2

| | Acid generator | Resin | Acid diffusion controller | Crosslinking agent | Other additives | Solvent |
|---|---|---|---|---|---|---|
| Example 16 | A-1 (1) a-2 (4) | B-9 (100) | E-3 (0.2) | — | — | S-4 (500) S-5 (100) |
| Example 17 | A-2 (4) | B-10 (100) | E-3 (0.15) | — | — | S-4 (500) S-5 (100) |
| Example 18 | A-1 (3) | B-11 (100) | E-3 (0.1) | — | — | S-4 (1200) |
| Example 19 | A-1 (3.5) | B-1 (100) | E-3 (0.1) | — | — | S-1 (400) S-3 (400) |
| Example 20 | A-1 (3) | C-1 (97) B-4 (3) | E-1 (0.1) | D-1 (7) | — | S-1 (550) S-3 (250) |
| Comparative Example 1 | a-1 (3) | B-1 (100) | E-5 (0.1) | — | — | S-1 (400) S-3 (400) |
| Comparative Example 2 | a-2 (3) | B-5 (100) | E-2 (0.1) | — | — | S-3 (700) S-6 (50) |
| Comparative Example 3 | a-3 (3) | B-5 (100) | E-2 (0.1) | — | — | S-3 (700) S-6 (50) |
| Comparative Example 4 | a-4 (5.5) | B-5 (100) | E-3 (0.1) | — | — | S-3 (700) S-6 (50) |
| Comparative Example 5 | a-5 (5.5) | B-5 (100) | E-3 (0.1) | — | — | S-3 (700) S-6 (50) |

(values in parenthesis are parts by weight)

TABLE 3

| | Thickness (Å) | PB Temperature (° C.) | PB Time (Sec.) | Exposure source | PEB Temperature (° C.) | PEB Time (Sec.) |
|---|---|---|---|---|---|---|
| Example 1 | 5,000 | 120 | 90 | KrF | 130 | 90 |
| Example 2 | 5,000 | 120 | 90 | KrF | 130 | 90 |
| Example 3 | 5,000 | 120 | 90 | KrF | 130 | 90 |
| Example 4 | 5,000 | 140 | 90 | KrF | 140 | 90 |
| Example 5 | 5,000 | 120 | 90 | KrF | 140 | 90 |
| Example 6 | 5,000 | 130 | 90 | KrF | 130 | 90 |
| Example 7 | 5,000 | 130 | 90 | KrF | 130 | 90 |
| Example 8 | 5,000 | 100 | 90 | KrF | 100 | 90 |
| Example 9 | 3,300 | 130 | 90 | ArF | 130 | 90 |
| Example 10 | 3,300 | 130 | 90 | ArF | 130 | 90 |
| Example 11 | 3,300 | 130 | 90 | ArF | 130 | 90 |
| Example 12 | 3,300 | 130 | 90 | ArF | 130 | 90 |

TABLE 3-continued

|  | Thickness (Å) | PB Temperature (°C.) | Time (Sec.) | Exposure source | PEB Temperature (°C.) | Time (Sec.) |
|---|---|---|---|---|---|---|
| Example 13 | 3,300 | 130 | 60 | ArF | 120 | 60 |
| Example 14 | 3,300 | 130 | 90 | ArF | 110 | 90 |
| Example 15 | 3,300 | 130 | 90 | ArF | 110 | 90 |
| Example 16 | 3,300 | 130 | 90 | ArF | 140 | 90 |
| Example 17 | 3,300 | 130 | 90 | ArF | 130 | 90 |
| Example 18 | 1,000 | 130 | 90 | F2 | 110 | 90 |
| Example 19 | 3,000 | 120 | 90 | Electron beam | 130 | 90 |
| Example 20 | 5,000 | 90 | 90 | KrF | 110 | 90 |
| Comparative Example 1 | 5,000 | 120 | 90 | KrF | 130 | 90 |
| Comparative Example 2 | 3,300 | 130 | 90 | ArF | 130 | 90 |
| Comparative Example 3 | 3,300 | 130 | 90 | ArF | 130 | 90 |
| Comparative Example 4 | 3,300 | 130 | 90 | ArF | 130 | 90 |
| Comparative Example 5 | 3,300 | 130 | 90 | ArF | 130 | 90 |

TABLE 4

|  | Resolution (μm) | Sensitivity | Mask pattern dependability | Nano edge roughness |
|---|---|---|---|---|
| Example 1 | 0.20 | 360 J/m$^2$ | Good | Good |
| Example 2 | 0.21 | 410 J/m$^2$ | Good | Good |
| Example 3 | 0.22 | 330 J/m$^2$ | Good | Good |
| Example 4 | 0.21 | 570 J/m$^2$ | Good | Good |
| Example 5 | 0.22 | 360 J/m$^2$ | Good | Good |
| Example 6 | 0.20 | 350 J/m$^2$ | Good | Good |
| Example 7 | 0.21 | 340 J/m$^2$ | Good | Good |
| Example 8 | 0.22 | 460 J/m$^2$ | Good | Good |
| Example 9 | 0.16 | 410 J/m$^2$ | Good | Good |
| Example 10 | 0.14 | 320 J/m$^2$ | Good | Good |
| Example 11 | 0.15 | 330 J/m$^2$ | Good | Good |
| Example 12 | 0.13 | 340 J/m$^2$ | Good | Good |
| Example 13 | 0.15 | 350 J/m$^2$ | Good | Good |
| Example 14 | 0.14 | 360 J/m$^2$ | Good | Good |
| Example 15 | 0.15 | 400 J/m$^2$ | Good | Good |
| Example 16 | 0.16 | 410 J/m$^2$ | Good | Good |
| Example 17 | 0.15 | 280 J/m$^2$ | Good | Good |
| Example 18 | 0.13 | 220 J/m$^2$ | Good | Good |
| Example 19 | 0.12 | 2.9 μC | Good | Good |
| Example 20 | 0.21 | 350 J/m$^2$ | Good | Good |
| Comparative Example 1 | 0.21 | 320 J/m$^2$ | Bad | Good |
| Comparative Example 2 | 0.15 | 220 J/m$^2$ | Bad | Bad |
| Comparative Example 3 | 0.16 | 420 J/m$^2$ | Good | Bad |
| Comparative Example 4 | 0.16 | 280 J/m$^2$ | Bad | Good |
| Comparative Example 5 | 0.14 | 360 J/m$^2$ | Good | Bad |

TABLE 5

|  | Acid generator | Resin | Acid diffusion controller | Solvent |
|---|---|---|---|---|
| Example 21 | A-4 (5) | B-1 (100) | E-5 (0.15) | S-1 (400) S-2 (400) |
| Example 22 | A-1 (2) a-1 (5) | B-2 (100) | E-5 (0.15) | S-1 (400) S-3 (400) |
| Example 23 | A-3 (2) a-1 (5) | B-3 (100) | E-3 (0.15) | S-1 (400) S-3 (400) |
| Example 24 | A-1 (2) a-6 (4) | B-4 (100) | E-1 (0.1) E-4 (0.1) | S-1 (400) S-3 (400) |
| Example 25 | A-2 (3) a-2 (1) | B-5 (100) | E-3 (0.15) | S-3 (700) S-6 (50) |
| Example 26 | A-1 (2) a-4 (3) | B-5 (100) | E-3 (0.1) | S-3 (700) S-6 (50) |
| Comparative Example 6 | a-1 (5) | B-1 (100) | E-5 (0.2) | S-1 (400) S-3 (400) |
| Comparative Example 7 | a-4 (5) | B-5 (100) | E-3 (0.2) | S-3 (700) S-6 (50) |
| Comparative Example 8 | a-5 (5) | B-5 (100) | E-3 (0.2) | S-3 (700) S-6 (50) |

(values in parenthesis are parts by weight)

TABLE 6

|  | Thickness (Å) | PB Temperature (°C.) | Time (Sec.) | Exposure source | PEB Temperature (°C.) | Time (Sec.) |
|---|---|---|---|---|---|---|
| Example 21 | 5,000 | 120 | 90 | KrF | 130 | 90 |
| Example 22 | 5,000 | 120 | 90 | KrF | 130 | 90 |
| Example 23 | 5,000 | 120 | 90 | KrF | 130 | 90 |
| Example 24 | 5,000 | 100 | 90 | KrF | 100 | 90 |
| Example 25 | 3,300 | 130 | 130 | ArF | 130 | 90 |
| Example 26 | 3,300 | 130 | 130 | ArF | 130 | 90 |
| Comparative Example 6 | 5,000 | 120 | 90 | KrF | 130 | 90 |
| Comparative Example 7 | 3,300 | 130 | 90 | ArF | 130 | 90 |
| Comparative Example 8 | 3,300 | 130 | 90 | ArF | 130 | 90 |

TABLE 7

|  | Resolution (μm) | Sensitivity | Mask pattern faithfulness | Nano edge roughness |
|---|---|---|---|---|
| Example 21 | 0.19 | 450 J/m$^2$ | 4 | Good |
| Example 22 | 0.18 | 400 J/m$^2$ | 7 | Good |
| Example 23 | 0.20 | 460 J/m$^2$ | 9 | Good |
| Example 24 | 0.21 | 400 J/m$^2$ | 6 | Good |
| Example 25 | 0.15 | 360 J/m$^2$ | 7 | Good |
| Example 26 | 0.14 | 300 J/m$^2$ | 5 | Good |
| Comparative Example 6 | 0.21 | 300 J/m$^2$ | 12 | Good |
| Comparative Example 7 | 0.16 | 240 J/m$^2$ | 10 | Good |
| Comparative Example 8 | 0.15 | 310 J/m$^2$ | 5 | Bad |

Tables 4 and 7 clearly show that the radiation sensitive resin composition using the acid generator (I) of the present invention excels in mask pattern dependability and mask pattern fidelity, excels in smoothness due to good nano edge roughness, and exhibits high sensitivity and resolution.

INDUSTRIAL APPLICABILITY

The acid generator (I) exhibits comparatively high combustibility, does not accumulate in the human body and exhibits high transparency to ultraviolet rays such as a KrF excimer laser, ArF excimer laser, F$_2$ excimer laser, or EUV and electron beams. The acid generator (I) is, therefore, useful as a photoacid generator that can generate the sulfonic acid (I-a) of the present invention in response to these radiations or to heat, particularly as a photoacid generator in a positive-tone radiation sensitive resin composition and negative-tone radiation sensitive resin composition useful for a chemically amplified resist.

Due to the presence of a strong fluorine-containing electron drawing group in the a-position of the sulfonic acid group, the sulfonate (I-a) possesses the characteristics of producing highly acidic sulfonic acid and the like, difficulty in sublimation during photolithography processing due to a high boiling point, and a moderately short acid diffusion length in the resist film. Also, since the fluorine content is less than that in the higher perfluoroalkanesulfonic acid, combustibility is comparatively high and accumulation in the human body is low.

The sulfonyl halide compound (I-b) of the present invention is particularly useful as a raw material or intermediate for synthesizing the acid generator (I).

The positive-tone radiation sensitive resin composition and negative-tone radiation sensitive resin composition containing the acid generator (I) effectively responds to deep ultraviolet rays typified by a KrF excimer laser, ArF excimer laser, $F_2$ excimer laser, or EUV and electron beams, exhibits excellent sensitivity, a sufficiently short diffusion length of acid in the resist film, excels in resolution, exhibits a small pattern density dependency, and excels in smoothness on the surface and sidewalls of the resist pattern. The resin composition is extremely useful in the field of microfabrication represented by manufacturing integrated circuit elements which are anticipated to be more and more miniaturized in the future.

The invention claimed is:

1. A sulfonyl halide compound shown by the following formula (I-b),

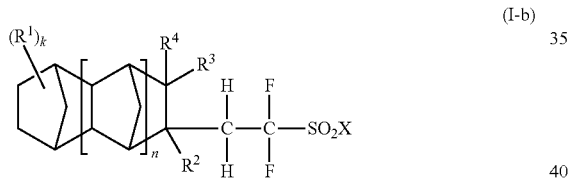

(I-b)

wherein $R^1$ represents —$R^5$, —$COR^6$, —$COOR^6$, —$CON(R^6)(R^7)$, —$N(R^6)(R^7)$, —$N(R^6)CO(R^7)$, —$N(R^6)COOR^7$, —$N(COR^6)(COR^7)$, —$SR^6$, —$SOR^6$, —$SO_2R^6$, or —$SO_2(OR^6)$, (wherein $R^5$ represents a substituted or unsubstituted, linear, branched, or cyclic monovalent hydrocarbon group having 1-30 carbon atoms, a substituted or unsubstituted aryl group having 6-30 carbon atoms, or a substituted or unsubstituted, monovalent hetero cyclic organic group having 4-30 carbon atoms, $R^6$ and $R^7$ individually represent a hydrogen atom, a substituted or unsubstituted, linear, branched, or cyclic monovalent hydrocarbon group having 1-30 carbon atoms, a substituted or unsubstituted aryl group having 6-30 carbon atoms, or substituted or unsubstituted, monovalent hetero cyclic organic group having 4-30 carbon atoms, provided that when both $R^6$ and $R^7$ are present in the group $R^1$, $R^6$ and $R^7$ may bond to form a ring), two or more $R^1$ groups, if present, may be either the same or different, the $R^1$ group may bond to form a ring with carbon atoms in the norbornene structure, and two or more $R^1$ groups may bond to form a ring; $R^2$, $R^3$, and $R^4$ individually represent a hydrogen atom or a linear, branched, or cyclic alkyl group having 1-30 carbon atoms; k is an integer of 0 or more; n is an integer of 0-5; and X is a halogen atom.

2. A positive-tone radiation sensitive resin composition comprising:
(A) a photoacid generator comprising an onium sulfonate compound shown by the following general formula (1),

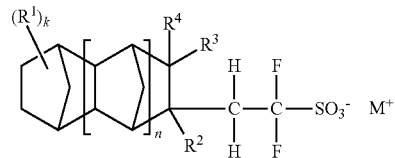

(1)

wherein $R^1$ represents —$R^5$, —$COR^6$, —$COOR^6$, —$CON(R^6)(R^7)$, —$N(R^6)(R^7)$, —$N(R^6)CO(R^7)$, —$N(R^6)COOR^7$, —$N(COR^6)(COR^7)$, —$SR^6$, —$SOR^6$, —$SO_2R^6$ or —$SO_2(OR^6)$, (wherein $R^5$ represents a substituted or unsubstituted, linear, branched, or cyclic monovalent hydrocarbon group having 1-30 carbon atoms, a substituted or unsubstituted aryl group having 6-30 carbon atoms, or a substituted or unsubstituted, monovalent hetero cyclic organic group having 4-30 carbon atoms, $R^6$ and $R^7$ individually represent a hydrogen atom, a substituted or unsubstituted, linear, branched, or cyclic monovalent hydrocarbon group having 1-30 carbon atoms, a substituted or unsubstituted aryl group having 6-30 carbon atoms, or substituted or unsubstituted, monovalent hetero cyclic organic group having 4-30 carbon atoms, provided that when both $R^6$ and $R^7$ are present in the group $R^1$, $R^6$ and $R^7$ may bond to form a ring), two or more $R^1$ groups, if present, may be either the same or different, the $R^1$ group may bond to form a ring with carbon atoms in the norbornene structure, and two or more $R^1$ groups may bond to form a ring; $R^2$, $R^3$, and $R^4$ individually represent a hydrogen atom or a linear, branched, or cyclic alkyl group having 1-30 carbon atoms; k is an integer of 0 or more; n is an integer of 0-5; and $M^+$ represents a monovalent onium cation; and (B) an acid-dissociable group-containing resin which is insoluble or scarcely soluble in alkali and becomes alkali soluble when the acid-dissociable group dissociates, and which includes a recurring unit of the formula (B1), (B2), and/or (B3) as follows:

(B1)

wherein $R^{23}$ individually represent a hydrogen atom or monovalent organic group, and c and d each represent an integer from 1-3,

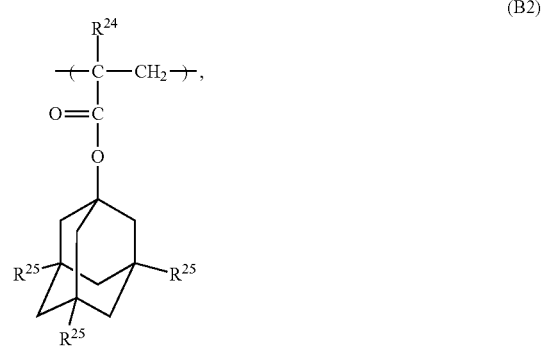

(B2)

-continued

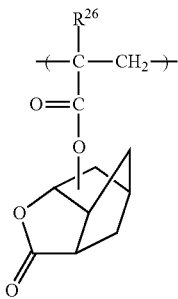
(B3)

wherein, as to formulas (B2) and (B3), $R^{24}$, and $R^{26}$ groups individually represent a hydrogen atom or methyl group and $R^{25}$ groups individually represent a hydrogen atom, hydroxyl group, cyano group, or —COOR$^{29}$, wherein R$^{29}$ represents a hydrogen atom, a linear or branched alley group having 1-4 carbon atoms, or a cycloalkyl group having 3-20 carbon atoms.

3. A negative-tone radiation sensitive resin composition comprising (A) a photoacid generator comprising:

an acid generator comprising an onium sulfonate compound shown by the following general formula (1),

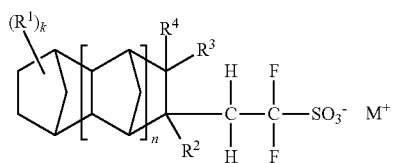
(1)

wherein $R^1$ represents —$R^5$, —$COR^6$, —$COOR^6$, —$CON(R^6)(R^7)$, —$N(R^6)(R^7)$, —$N(R^6)CO(R^7)$, —$N(R^6)COOR^7$, —$N(COR^6)(COR^7)$, —$SR^6$, —$SOR^6$, —$SO_2R^6$, or —$SO_2(OR^6)$, (wherein $R^5$ represents a substituted or unsubstituted, linear, branched, or cyclic monovalent hydrocarbon group having 1-30 carbon atoms, a substituted or unsubstituted aryl group having 6-30 carbon atoms, or a substituted or unsubstituted, monovalent hetero cyclic organic group having 4-30 carbon atoms, $R^6$ and $R^7$ individually represent a hydrogen atom, a substituted or unsubstituted, linear, branched, or cyclic monovalent hydrocarbon group having 1-30 carbon atoms, a substituted or unsubstituted aryl group having 6-30 carbon atoms, or substituted or unsubstituted, monovalent hetero cyclic organic group having 4-30 carbon atoms, provided that when both $R^6$ and $R^7$ are present in the group $R^1$, $R^6$ and $R^7$ may bond to form a ring), two or more $R^1$ groups, if present, may be either the same or different, the $R^1$ group may bond to form a ring with carbon atoms in the norbornene structure, and two or more $R^1$ groups may bond to form a ring; $R^2$, $R^3$, and $R^4$ individually represent a hydrogen atom or a linear, branched, or cyclic alkyl group having 1-30 carbon atoms; k is an integer of 0 or more; n is an integer of 0-5; and M$^+$ represents a monovalent onium cation, (C) an alkali soluble resin, and (D) a compound which can crosslink the alkali soluble resin in the presence of an acid.

\* \* \* \* \*